(12) United States Patent
Diebold et al.

(10) Patent No.: US 10,288,546 B2
(45) Date of Patent: *May 14, 2019

(54) MULTI-MODAL FLUORESCENCE IMAGING FLOW CYTOMETRY SYSTEM

(71) Applicant: OMEGA BIOSYSTEMS INCORPORATED, Los Angeles, CA (US)

(72) Inventors: Eric D. Diebold, Los Angeles, CA (US); Keegan Owsley, Los Angeles, CA (US); Jonathan Lin, Los Angeles, CA (US)

(73) Assignee: OMEGA BIOSYSTEMS INCORPORATED, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/058,734

(22) Filed: Aug. 8, 2018

(65) Prior Publication Data

US 2018/0348113 A1 Dec. 6, 2018

Related U.S. Application Data

(63) Continuation of application No. 15/292,582, filed on Oct. 13, 2016, now Pat. No. 10,078,045.
(Continued)

(51) Int. Cl.
*G01N 21/64* (2006.01)
*G01N 15/14* (2006.01)
(Continued)

(52) U.S. Cl.
CPC ......... *G01N 15/1434* (2013.01); *G01N 15/14* (2013.01); *G01N 15/147* (2013.01);
(Continued)

(58) Field of Classification Search
CPC .......... G01N 15/1434; G01N 15/1429; G01N 21/645; G01N 15/1425; G01N 15/1475;
(Continued)

(56) References Cited

U.S. PATENT DOCUMENTS 4,883,656 A 11/1989 Konrad et al.
5,111,332 A 5/1992 Kuwabara et al.
(Continued)

FOREIGN PATENT DOCUMENTS

DE 102010044013 5/2012
JP 11-006719 1/1999
(Continued)

OTHER PUBLICATIONS

Bectold et al., "Beam shaping and high-speed, cylinder-lens-free beam guiding using acousto-toptical deflectors without additional compensation optics," 2013, Optics Express, vol. 21, No. 12, pp. 14627-14635.
(Continued)

*Primary Examiner* — Kiho Kim
(74) *Attorney, Agent, or Firm* — Bret E. Field; Bozicevic, Field & Francis LLP

(57) ABSTRACT

In one aspect, the present teachings provide a system for performing cytometry that can be operated in three operational modes. In one operational mode, a fluorescence image of a sample is obtained by exciting one or more fluorophore(s) present in the sample by an excitation beam formed as a superposition of a top-hat-shaped beam with a plurality of beams that are radiofrequency shifted relative to one another. In another operational mode, a sample can be illuminated successively over a time interval by a laser beam at a plurality of excitation frequencies in a scanning fashion. The fluorescence emission from the sample can be detected and analyzed, e.g., to generate a fluorescence image of the
(Continued)

sample. In yet another operational mode, the system can be operated to illuminate a plurality of locations of a sample concurrently by a single excitation frequency, which can be generated, e.g., by shifting the central frequency of a laser beam by a radiofrequency. For example, a horizontal extent of the sample can be illuminated by a laser beam at a single excitation frequency. The detected fluorescence radiation can be used to analyze the fluorescence content of the sample, e.g., a cell/particle.

19 Claims, 27 Drawing Sheets

Related U.S. Application Data

(60) Provisional application No. 62/240,894, filed on Oct. 13, 2015.

(51) Int. Cl.
G02B 21/06 (2006.01)
G01N 15/10 (2006.01)

(52) U.S. Cl.
CPC ..... *G01N 15/1425* (2013.01); *G01N 15/1429* (2013.01); *G01N 15/1475* (2013.01); *G01N 21/645* (2013.01); *G02B 21/06* (2013.01); G01N 2015/1006 (2013.01); G01N 2015/1447 (2013.01); G01N 2015/1454 (2013.01); G01N 2021/6482 (2013.01)

(58) Field of Classification Search
CPC ......... G01N 15/147; G01N 2015/1006; G01N 2021/6482; G01N 2015/1454; G01N 2015/1447; G01N 15/14; G02B 21/06
See application file for complete search history.

(56) References Cited

U.S. PATENT DOCUMENTS

| | | | |
|---|---|---|---|
| 5,192,870 A | 3/1993 | Batchelder et al. | |
| 5,293,213 A | 3/1994 | Klein et al. | |
| 5,296,911 A | 3/1994 | Weyrauch | |
| 5,485,530 A | 1/1996 | Lakowicz et al. | |
| 5,504,337 A | 4/1996 | Lakowicz et al. | |
| 6,016,196 A | 1/2000 | Mermelstein | |
| 6,057,814 A | 5/2000 | Kalt | |
| 6,236,454 B1 | 5/2001 | Almogy | |
| 6,252,669 B1 | 6/2001 | Drabarek | |
| 6,271,924 B1 | 8/2001 | Ngoi et al. | |
| 6,297,884 B1 | 10/2001 | Drabarek | |
| 6,396,069 B1 | 5/2002 | MacPherson | |
| 6,592,822 B1 | 7/2003 | Chandler | |
| 6,867,899 B2 | 3/2005 | Knebel | |
| 7,400,457 B1 | 7/2008 | Cayer | |
| 7,630,063 B2 | 12/2009 | Padmanabhan et al. | |
| 7,724,426 B2 | 5/2010 | Yamashita et al. | |
| 7,889,348 B2 | 2/2011 | Tearney et al. | |
| 8,184,279 B2 | 5/2012 | Feldkhun | |
| 8,253,938 B2 | 8/2012 | Vacca et al. | |
| 9,201,011 B2 | 12/2015 | Kalkbrenner et al. | |
| 9,423,353 B2 | 8/2016 | Diebold et al. | |
| 2003/0031352 A1 | 2/2003 | Nelson et al. | |
| 2003/0226977 A1 | 12/2003 | Storz et al. | |
| 2005/0081245 A1 | 4/2005 | Arad et al. | |
| 2005/0121603 A1 | 6/2005 | Seyfried et al. | |
| 2008/0012919 A1 | 6/2008 | Vaughan | |
| 2008/0129298 A1 | 6/2008 | Vaughan et al. | |
| 2008/0285606 A1 | 11/2008 | Kippenberg et al. | |
| 2009/0219607 A1* | 9/2009 | Saggau | G02B 21/0016 359/305 |
| 2009/0237289 A1 | 9/2009 | Stoddard | |
| 2009/0323061 A1 | 12/2009 | Novotny et al. | |
| 2010/0210952 A1 | 8/2010 | Taira et al. | |
| 2010/0301024 A1 | 12/2010 | Unrath | |
| 2011/0192991 A1 | 8/2011 | Fukumoto et al. | |
| 2011/0317910 A1 | 12/2011 | Suzuki | |
| 2012/0270306 A1 | 10/2012 | Vacca et al. | |
| 2012/0294319 A1 | 11/2012 | Maleki et al. | |
| 2012/0307244 A1 | 12/2012 | Sharpe et al. | |
| 2015/0177133 A1 | 6/2015 | Choi et al. | |
| 2016/0003741 A1 | 1/2016 | Diebold | |
| 2017/0227444 A1 | 8/2017 | Jalai et al. | |
| 2017/0268981 A1 | 9/2017 | Diebold et al. | |

FOREIGN PATENT DOCUMENTS

| | | |
|---|---|---|
| JP | 2008-9395 | 1/2008 |
| JP | 2009-20492 | 1/2009 |
| JP | 2009-509684 | 3/2009 |
| JP | 2011-158413 | 8/2011 |
| JP | 2011-191496 | 9/2011 |
| WO | WO 93/09423 | 5/1993 |
| WO | WO 03/29882 | 4/2003 |
| WO | WO 2007/041412 | 4/2007 |
| WO | WO 2007066126 | 6/2007 |
| WO | WO 2009087392 | 7/2009 |
| WO | WO 2011/023593 | 3/2011 |
| WO | WO 2012/127907 | 9/2012 |
| WO | WO 2014110290 | 7/2014 |
| WO | WO 2014152048 | 9/2014 |
| WO | WO2015143041 | 9/2015 |
| WO | WO 2016054293 | 4/2016 |
| WO | WO 2017066404 | 4/2017 |
| WO | WO2017161247 | 9/2017 |

OTHER PUBLICATIONS

Bertero et al. "Iterative image reconstruction: a point of view," Proceedings of the Interdisciplinary Workshop on Mathematical Methods in Biomedical Imaging and Intensity-Modulated Radiation Therapy (IMRT), Oct. 31, 2007, pp. 1-25.

Diebold et al. "Digitally synthesized beat frequency multiplexing for sub-millisecond fluorescence microscopy," Nature Photonics, Oct. 2013, vol. 7, No. 10, pp. 806-810, published online Sep. 22, 2013.

Digman et al. "Fluorescence correlation spectroscopy and fluorescence cross-correlation spectroscopy," Wiley Interdisciplinary Reviews, Systems Biology and Medicine, vol. 1, No. 2, Apr. 29, 2009, pp. 273-282.

Dutta et al. "Quantitative Statistical Methods for Image Quality Assessment," Theranostics, vol. 3, No. 10, Oct. 4, 2013, pp. 741-756.

Eisenstein, M. "Fluorescence microscopy gets a frequency boost", Nature Methods, Dec. 2013, vol. 10, No. 12, p. 1149.

Fessler, J. A. "Penalized weighted least-squares image reconstruction for positron emission tomography," IEEE Trans. Medical Imaging, vol. 13, No. 2, Jun. 1994, pp. 290-300.

Hanley et al. "Fluorescence lifetime imaging in an optically sectioning programmable array microscope (PAM)", Cytometry, Part A, vol. 67A, No. 2, Jan. 1, 2005, pp. 112-118.

Hoffman, Robert A. "Pulse Width for Particle Sizing," Current Protocols in Cytometry, 50, Unit 1.23, pp. 1.23.1-1.23.17 (Oct. 2009).

International Search Report and Written Opinion for PCT Application PCT/US2014/010928 dated May 1, 2014, date of complete Apr. 28, 2014.

Office Action dated Mar. 22, 2016 for U.S. Appl. No. 14/792,282.

Sisan et al. "Event Ordering in Live-Cell Imaging Determined from Temporal Cross-Correlation Asymmetry," Biophysical Journal, vol. 98, No. 11, Jun. 1, 2010, pp. 2432-2441.

Subramaniam et al. "Photophysics of Green and Red Fluorescent Proteins: Implications for Quantitative Microscopy", Methods in Enzymology, vol. 360, Jan. 1, 2003, pp. 178-201.

Thews et al. "Cross Talk Free Fluorescence Cross Correlation Spectroscopy in Live Cells," Biophysical Journal, vol. 89, No. 3, Sep. 30, 2005, pp. 2069-2076.

(56) References Cited

OTHER PUBLICATIONS

Varma et al. "Fast image reconstruction for fluorescence microscopy," AIP Advances, vol. 2, No. 3, Sep. 17, 2012, pp. 32174-32174.

Wu et al. "Frequency Division Multiplexed Multichannel High-Speed Fluorescence Confocal Microscope," Biophysical Journal, vol. 91, Sep. 2006, pp. 2290-2296.

\* cited by examiner

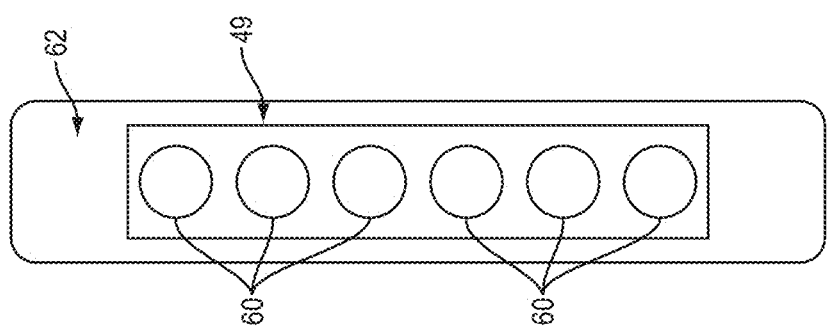

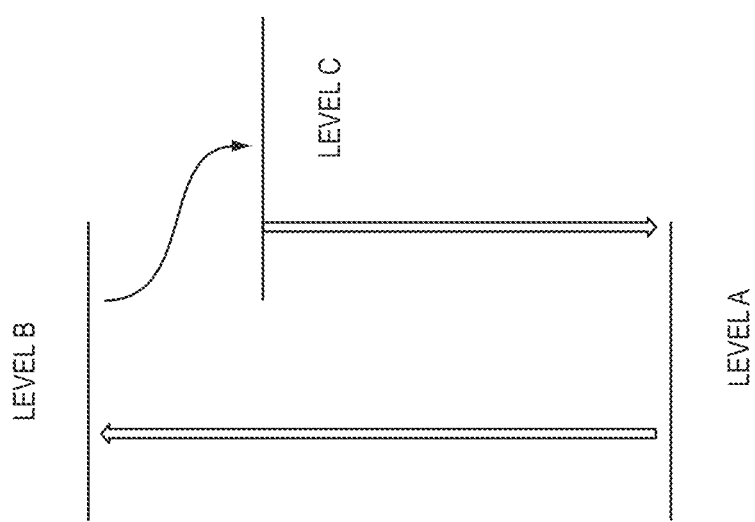

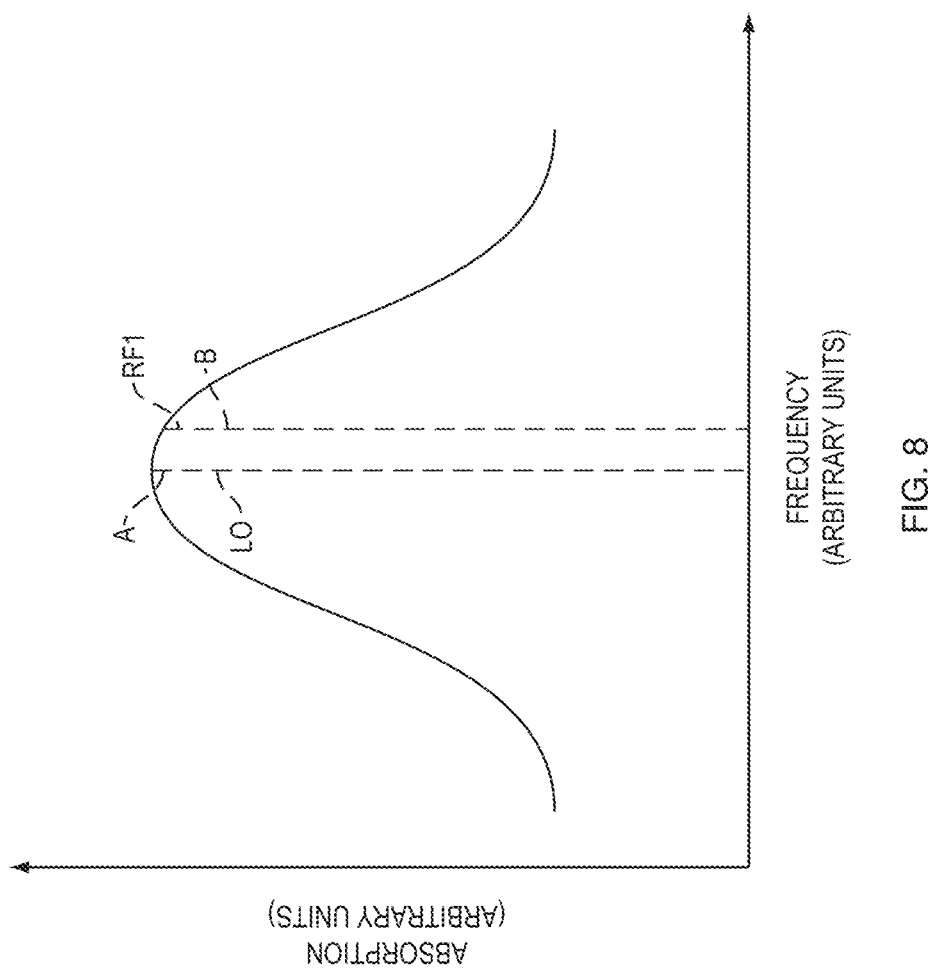

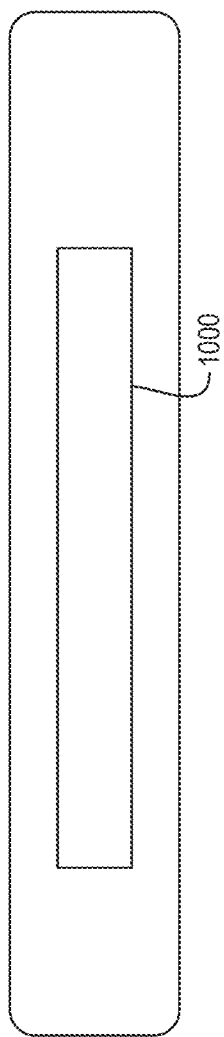

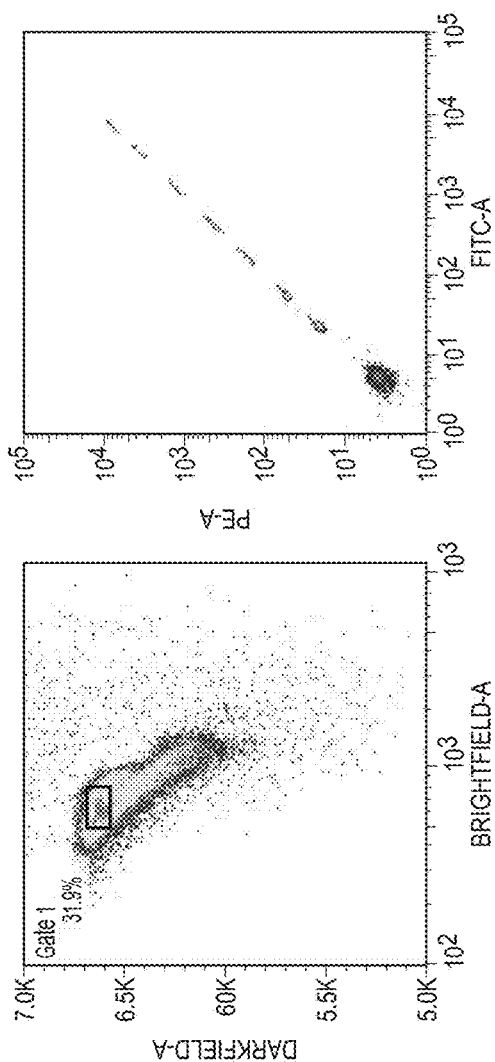
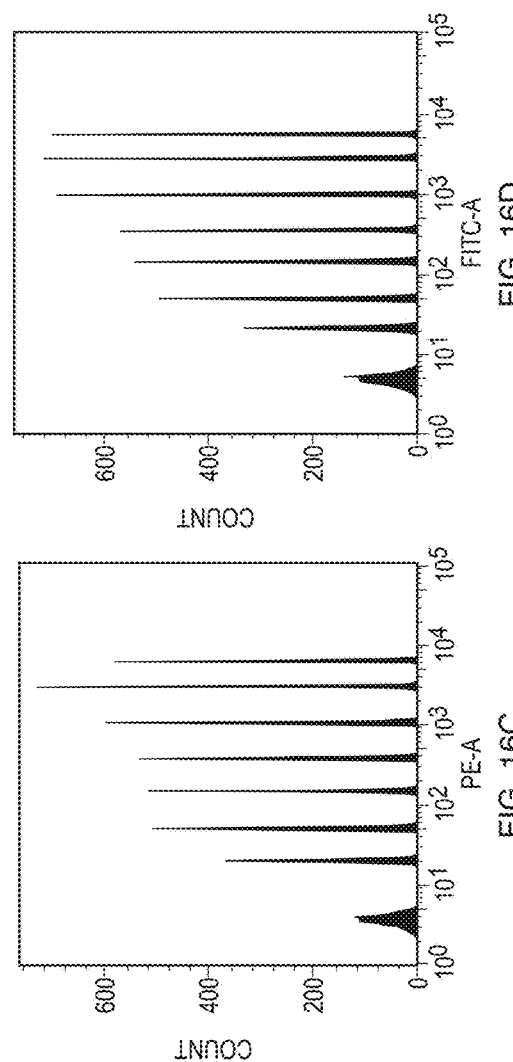
FIG. 16A
FIG. 16B
FIG. 16C
FIG. 16D

MULTI-MODAL FLUORESCENCE IMAGING FLOW CYTOMETRY SYSTEM

CROSS REFERENCE TO RELATED APPLICATION

This application claims priority to Provisional Patent Application No. 62/240,894, filed Oct. 13, 2016, the contents of which are incorporated herein by reference in their entireties.

BACKGROUND

The present invention relates generally to devices and methods for fluorescence analysis of samples, and more particularly to devices and methods for fluorescence-based flow cytometry.

Fluorescence imaging has a variety of biomedical applications, for example, in obtaining information regarding molecular composition of biological specimens. In biomedical flow cytometry, fluorescence radiation emitted by exogenous and/or endogenous cellular fluorophores is collected and analyzed to derive information about chemical and/or physical properties of cells.

In conventional fluorescence-based flow cytometry, however, the acquisition of blur-free images of cells flowing at a high speed, or other fast phenomena such as sub-millisecond biochemical dynamics, can be challenging. In particular, the weak optical emission of many fluorophores coupled with the short exposure of the sample at imaging frame rates in the kilohertz range renders the acquisition of blur-free images difficult. Moreover, many conventional systems operate in only one imaging mode and hence fail to provide sufficient flexibility for sample analysis.

Accordingly, there is a need for enhanced methods and systems for fluorescence analysis, and in particular a need for enhanced methods and systems for performing fluorescence-based flow cytometry.

SUMMARY

In one aspect, a system for performing cytometry is disclosed, which comprises a laser for generating a laser beam having a central frequency suitable for exciting at least one fluorophore, an acousto-optic deflector for receiving the laser beam and generating a plurality of angularly separated laser beams each having a radio frequency (RF) shift relative to said central frequency. The angularly separated laser beams include a local oscillator beam (LO beam) and a plurality of RF comb beams, where each of the beams exhibits a radiofrequency shift relative to the central laser frequency. An optical element directs the LO beam along a propagation path different than propagation paths of the RF comb beams. A top-hat beam shaper receives the LO beam and imparts thereto a top-hat intensity profile, e.g., along one direction in a plane perpendicular to its propagation direction. The system further includes a beam splitter that receives the top-hat-shaped LO beam and the RF comb beams and provides a combined beam by spatial overlap of said beams, and at least one optical element (e.g., a lens) for directing the combined beam onto a sample, which can comprise a plurality of cells at least some of which are associated with said fluorophore, such that LO beam concurrently illuminates a plurality of spatial locations of the sample, e.g., as the sample flows through a flow cell, and each of said RF comb beams illuminates a different one of said spatial locations to elicit fluorescence radiation from said fluorophore, if present, at said spatial locations. The fluorescence radiation emitted from each of said sample locations exhibits a beat frequency corresponding to a frequency difference between said LO beam and one of the RF comb beams illuminating that sample location.

In some embodiments, the frequency differences between the radiofrequency (RF) shifts are less than a FWHM (full width at half maximum) of a spectral absorption peak of said fluorophore. By way of example, the radio frequency shifts are in a range of about 10 MHz to about 250 MHz, e.g., in a range of about 50 MHz to about 150 MHz. In some embodiments, the radiofrequency shifts are separated from one another by a frequency in a range of about 0.1 MHz to about 4 MHz In some embodiments, the above system further comprises a lens disposed downstream of the beam splitter for focusing the top-hat-shaped LO beam and the RF comb beams onto an intermediate plane such that the top-hat LO beam has overlap with each of the RF comb beams. The top-hat-shaped LO beam's intensity profile at each overlap location can be substantially identical with its profile at another overlap location. In some cases, the LO beam has a linear extent in this intermediate plane (e.g., an extent along a horizontal dimension in this plane) that is substantially equal to a linear extent of the angularly separated RF comb beams (e.g., the maximum horizontal distance between the RF comb beams). The top-hat-shaped LO beam has preferably a substantially uniform polarization in the top-hat direction (along the elongated direction of the beam).

By way of example, in some embodiments, the RF comb beams have a Gaussian intensity profile, and the top-hat-shaped LO beam has an intensity that is substantially equal to the maximum intensity of the Gaussian intensity profile. Further, the polarizations of the RF comb beams and the top-hat shaped LO beam can be aligned.

The system can include a radio frequency generator for concurrently generating radio frequencies corresponding to the radio frequency shifts and applying the radio frequencies to the acousto-optic deflector to generate said LO and RF comb beams. In some embodiments, the radio frequency generator includes a direct digital synthesizer (DDS) RF comb generator. In some embodiments, an electronic power amplifier can amplify the radiofrequency drive signals generated by the radiofrequency generator for application to the acousto-optic deflector. A controller can control the radiofrequency generator, e.g., for operating the system in different operational modes, as discussed further below, and/or for adjusting the amplitude and/or frequency of the drive signals applied to the acousto-optic deflector.

The system can further include one or more photodetectors (e.g., one or more photomultiplier tubes) for detecting the fluorescence radiation, if any, emitted from the sample and generating a time-domain fluorescence signal. In some cases, an appropriate filter (e.g., an optical bandpass filter) is disposed in front of the photodetector to allow transmission of a fluorescence frequency of interest while blocking unwanted radiation frequencies.

In some embodiments, the excitation radiation (i.e., the combination of the LO beam and the RF comb beams) can concurrently excite multiple fluorophores within the sample. In some such embodiments, the system can include multiple photodetectors, each of which is used to detect fluorescence radiation emitted from one of those fluorophores. In some embodiments, an appropriate filter, e.g., a bandpass filter, is disposed in front of each of the photodetectors that allows transmission of radiation at the fluorescence frequency of interest to the respective detector while blocking unwanted radiation.

In some embodiments, an objective lens can receive the excitation radiation (i.e., the combination of the LO beam and the RF comb beams) via reflection by a dichroic mirror and can focus the excitation radiation onto a sample under study. The fluorescence radiation emitted by the sample can pass through the objective lens and the dichroic mirror to be focused via one or more lenses onto the photodetector. In some embodiments in which multiple fluorescence frequencies corresponding to fluorescence emission from multiple fluorophores within the sample are detected via a plurality of photodetectors (e.g., photomultiplier tubes), each photodetector can be associated with an appropriate dichroic mirror from which it receives, via reflection, fluorescence radiation having a frequency corresponding to fluorescence emission from one of the fluorophores. The dichroic mirror can allow fluorescence frequencies corresponding to the other fluorophores to pass through to be detected by other downstream detectors.

In some embodiments, the fluorescence radiation emitted by the sample can be coupled, e.g., via one or more lenses, to an optical fiber. The optical fiber can extend from a proximal end, which receives the fluorescence radiation, to a distal end at which the radiation exits the optical fiber. In some embodiments, an output lens optically coupled to the distal end of the optical fiber facilitates directing the fluorescence radiation exiting the optical fiber onto one or more photodetectors.

The system further includes an analysis module in communication with one or more photodetectors to receive one or more time-domain fluorescence signals from the photodetector(s) and to reconstruct one or more fluorescence images of the sample. For example, the analysis module can provide frequency de-multiplexing of the fluorescence signal to determine the beat frequencies and can generate a fluorescence image of the sample by correlating the beat frequencies with spatial locations of the sample emitting fluorescence radiation modulated at those beat frequencies. By way of example, in some embodiments, those spatial locations can be along a horizontal dimension of the sample. In some embodiments, as the sample flows through the flow cell, fluorescence radiation from different portions of the sample (e.g., different horizontal extents of the sample) is collected and analyzed to generate a two-dimensional fluorescence image of the sample.

In some embodiments, the analysis module reconstructs a fluorescence image of the sample by (1) obtaining a Fourier transform (e.g., FFT) of at least a portion of the fluorescence signal to obtain frequency components of the signal, which correspond to the beat frequencies, (2) for each frequency component (beat frequency), computing a measure of amplitude of that frequency component, e.g., by obtaining the square root of the sum of squares of the real and imaginary parts of that frequency component, to provide a pixel value corresponding to a location of the image corresponding to that beat frequency.

In some embodiments, the analysis module is configured to effect the frequency de-multiplexing of the detected fluorescence signal by digitizing the fluorescence signal, e.g., after amplification, and generating several copies of the digitized fluorescence signal, where the number (N) of the digitized copies corresponds to the number of frequencies associated with RF comb beams. Each digitized copy of the fluorescence signal is multiplied with sine and cosine waves having a frequency corresponding to a beat frequency equal to a difference between the frequencies of one of the RF comb beams and the LO beam to generate a plurality of intermediate signals. Each intermediate signal is passed through a low-pass filter having a bandwidth equal to one half of the frequency spacing between the RF comb frequencies. For each beat frequency corresponding to one of the RF comb frequencies, the square root of the sum of the squares of the two filtered intermediate signals corresponding to that frequency is obtained as a measure of the amplitude of an image pixel corresponding to the sample location illuminated by the LO beam and the RF comb beam that emits fluorescence radiation exhibiting modulation at that beat frequency.

In some embodiments, the analysis module is configured to effect the frequency de-multiplexing of the detected fluorescence signal by generating several copies of the digitized fluorescence signal, where the number (N) of the digitized copies corresponds to the number of frequencies associated with the RF comb beams. Each copy of the digitized fluorescence signal is filtered by passing that signal through a bandpass filter centered at a beat frequency associated with one of the RF comb beams. An envelope detector is employed to estimate the amplitude of each pixel corresponding to that frequency.

In some embodiments, the above system further includes a detection arm for generating a brightfield image of the sample and another detection arm for generating a darkfield image of the sample. The brightfield detection arm can be positioned, e.g., relative to a flow cell through which the sample flows so as to receive the excitation radiation (i.e., the combined LO and RF comb beams) in a forward direction, that is, along a direction substantially parallel to the propagation direction of the excitation radiation as it enters the flow cell. Further, the darkfield detection arm can be positioned, e.g., relative to the flow cell so as to receive excitation radiation scattered by the sample along a direction substantially orthogonal to the propagation direction of the excitation radiation as it enters the flow cell.

In some embodiments, each of the brightfield and darkfield detection arms includes one or more lenses for focusing radiation transmitted through the flow cell or radiation scattered by the sample in a direction different than the propagation direction of the excitation radiation, respectively, onto a photodetector, e.g., a photomultiplier tube. In some cases, an appropriate filter, e.g., a bandpass filter, can be placed in front of the photodetector to allow passage of desired radiation frequencies (e.g., excitation frequencies) while blocking unwanted radiation frequencies.

In some cases, the analysis module is configured to generate a composite image via overlay of the brightfield and/or the darkfield and the fluorescence image.

In a related aspect, a method of flow cytometry is disclosed, which includes generating an excitation beam by superimposing a top-hat-shaped laser beam (LO beam) with a plurality of laser beams that are radiofrequency shifted from one another (RF comb beams), wherein the excitation beam is capable of eliciting fluorescence from at least one fluorophore, and directing the excitation beam onto a sample so as to excite said fluorophore, if present in the sample, to cause it to emit fluorescence radiation. The superposition of the LO beam and the RF comb beams results in spatial encoding of a plurality of beat frequencies corresponding to frequency differences between the RF comb beams and the LO beam. The fluorescence radiation is detected and frequency de-multiplexed so as to generate a fluorescence image of the sample.

In some embodiments, a brightfield image and a darkfield image of the sample are generated, which can supplement the information provided by the fluorescence image. In some embodiments, the above system further includes a subsystem for performing fluorescence lifetime measurement of the fluorophores at multiple spatial locations on the sample to form a fluorescence lifetime image. The subsystem includes a photodetector for detecting the combined excitation beam and generating an excitation signal in response to said detection. The analysis module is in communication with the photodetector to receive the detected excitation signal and to de-multiplex the beat frequencies associated with the excitation signal to determine the phase of each of the beat frequencies at each spatial location on the sample. The analysis module is further configured to determine the phase of each of the beat frequencies associated with the detected fluorescence signal and to compare the phase of each frequency associated with the combined excitation beam with the phase of the respective beat frequency associated with the fluorescence signal to perform fluorescence lifetime measurement at multiple spatial locations on the sample.

In a related aspect, a system for performing flow cytometry is disclosed, which comprises a laser for generating a laser beam having a frequency suitable for exciting at least one fluorophore, an acousto-optic deflector (AOD), preferably a single acousto-optic deflector, configured to receive said laser beam, a radio-frequency generator for applying one or more drive signals to said AOD, and a controller for controlling said radio-frequency generator so as to provide three operational modes. The operational modes include a first operational mode in which said controller effects the frequency generator to apply concurrently a plurality of radiofrequency drive signals to said AOD so as to generate a plurality of radiofrequency shifted beams for concurrently illuminating a plurality of spatial locations of a sample, a second operational mode in which said controller effects the frequency generator to successively apply a plurality of radiofrequency drive signals to said AOD to illuminate the sample with a plurality of radiofrequency shifted beams at different times, and a third operational mode in which said controller effects the frequency generator to apply a single radiofrequency drive signal to said AOD to illuminate the sample with a beam at a single frequency. In certain embodiments, the spatial locations illuminated by the radiofrequency shifted beams are positioned along a single dimension, such that the radiofrequency shifted beams irradiate two or more positions along a single plane. For example, the radiofrequency shifted beams may illuminate spatial locations along a plane that is orthogonal to the longitudinal axis of the flow stream. Each radiofrequency shifted beam may be spaced apart from each other at the sample (e.g., at the surface of a flow stream) by 0.001 µm or more, such as by 0.005 µm or more, such as by 0.01 µm or more, such as by 0.05 µm or more, such as by 0.01 µm or more, such as by 0.05 µm or more, such as by 0.1 µm or more, such as by 0.5 µm or more, such as by 1 µm or more, such as by 2 µm or more, such as by 3 µm or more, such as by 5 µm or more, such as by 10 µm or more, such as by 15 µm or more, such as by 25 µm or more and including by 50 µm or more.

In a related aspect, the system can include an optical element for receiving one of the radio-frequency shifted beams (herein "local oscillator (LO) beam") and directing said LO beam along a propagation path different than propagation paths of the other frequency shifted beams (herein "RF comb beams"). The system can further include a top-hat beam shaper for imparting a top-hat intensity profile to the LO beam and one or more optical elements for combining the top-hat shaped LO beam with the RF comb beams in the first operational mode to form a composite excitation beam for illuminating the sample.

Further understanding of various aspects of the invention can be obtained by reference to the following detailed description in conjunction with the associated drawings, which are described briefly below.

BRIEF DESCRIPTION OF THE DRAWINGS

FIG. 16A is a scatter plot of darkfield intensity versus brightfield intensity of polystyrene beads stained with 8 discrete level of fluorescence dyes obtained by using a cytometry system in accordance with an embodiment of the present teachings, FIG. 16B shows a scatter plot of red fluorescence (PE) v. green fluorescence (FITC) emitted by a plurality of the polystyrene beads, where the data was obtained by using the rectangular section of the plot shown in FIG. 16A as a gate, FIGS. 16C and 16D are histograms corresponding to the data shown in FIG. 16B.

DETAILED DESCRIPTION

The present teachings relate generally to methods and systems for performing fluorescent analysis of samples. As discussed below, in some embodiments, a system according to the present teachings can operate in three operational modes for performing cytometry. Various terms used below to describe the present teachings have their ordinary meanings in the art, unless stated otherwise. For example, the term "fluorophore" is used herein consistent with its customary meaning in the art to refer to a fluorescent chemical compound that can emit radiation in response to illumination by excitation radiation.

The terms "cytometry" and "flow cytometry" are also used consistent with their customary meanings in the art. In particular, the term "cytometry" can refer to a technique for identifying and/or sorting or otherwise analyzing cells. The term "flow cytometry" can refer to a cytometric technique in which cells present in a fluid flow can be identified, and/or sorted, or otherwise analyzed, e.g., by labeling them with fluorescent markers and detecting the fluorescent markers via radiative excitation. The terms "about" and "substantially" are used herein to denote a maximum variation of 10%, or 5%, with respect to a property including numerical values.

Figure 1:
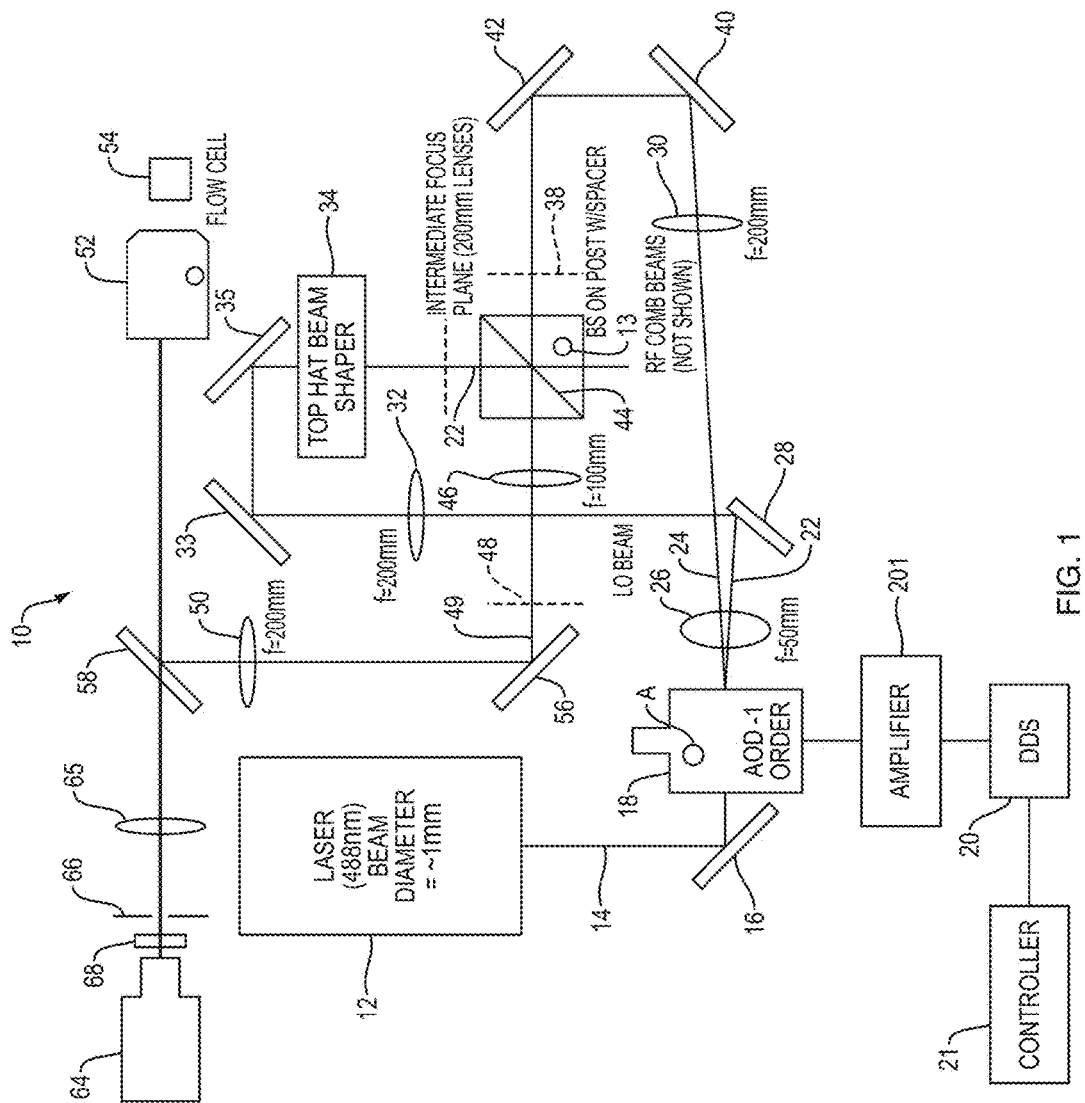
FIG. 1 schematically depicts a system in accordance with an embodiment of the invention.

FIG. 1 schematically depicts a system 10 for performing cytometry according to an embodiment of the present teachings, which can be operated in three operational modes. As discussed in more detail below, in one operational mode, a sample under study can be illuminated concurrently with a plurality of excitation frequencies, each of which can be obtained, e.g., by shifting the central frequency of a laser beam. More specifically, a plurality of sample locations can be concurrently illuminated by a laser beam that is generated by mixing a reference laser beam (herein also referred to as a local oscillator beam) with a plurality of radiofrequency-shifted laser beams such that each sample location is illuminated by the reference beam and one of the radiofrequency-shifted beams to excite a fluorophore of interest at that location, if present. In some embodiments, the reference beam can itself be generated via radiofrequency shifting of a laser beam. Thus, each spatial location of the sample can be "tagged" with a different beat frequency corresponding to a difference between the frequency of the reference beam and that of one of the radiofrequency-shifted beams. In other words, the fluorescence radiation emitted by the fluorophore will spatially encode the beat frequencies. The fluorescence emission can be detected and its frequency components can be analyzed to construct a fluorescence image of the sample.

In another operational mode, a sample can be illuminated successively over a time interval by a laser beam at a plurality of excitation frequencies. In some such embodiments, the excitation frequencies can be obtained by applying a time-varying drive signal to an acousto-optic deflector (AOD), which receives a laser beam. In many embodiments, the laser beam has a frequency in the hundreds of terahertz (THz) range, e.g., in a range of about 300 THz to about 1000 THz. The drive signal applied to the AOD is typically in the radiofrequency range, e.g., in a range of about 10 MHz to about 250 MHz. The passage of the laser beam through the AOD generates a plurality of diffracted beams, each corresponding to a different diffraction order. While the zero$^{th}$ diffracted beam exhibits no frequency shift relative to the frequency of the input laser beam, the higher-order diffracted beams exhibit a frequency shift relative to the frequency of the input laser beam corresponding to the frequency of the drive signal or a multiple thereof. In some embodiments, the first order diffracted beam having a frequency corresponding to the frequency of the input laser beam shifted by the drive signal is employed as the excitation beam for exciting a fluorophore of interest, if present in a sample under analysis. As the drive signal varies over time, the frequency and angular shift of the first-order diffracted beam also varies, thereby allowing the illumination of the sample at different excitation frequencies at different locations. The fluorescence emission, if any, from each illuminated location can be collected and analyzed to construct a fluorescence image of the sample.

In yet another operational mode, the system 10 can be operated to illuminate a plurality of locations of a sample concurrently by a single excitation frequency, which can be generated, e.g., by shifting the central frequency of a laser beam by a radiofrequency. For example, a horizontal extent of the sample can be illuminated by a laser beam at a single excitation frequency. The detected fluorescence radiation can be used to analyze the fluorescence content of the sample, e.g., a cell/particle.

Thus, one advantage of system 10, among others discussed below, is that it provides significant flexibility in obtaining fluorescence emission data in different modes without a need to utilize different instruments or to make any mechanical modifications to the system when switching between different operational modes.

In certain embodiments, systems include one or more light sources. In some instances, the light source is a narrow band light source, including but not limited to a narrow wavelength LED, laser or a broadband light source coupled to one or more optical bandpass filters, diffraction gratings, monochromators or any combination thereof which in combination produces a narrow band of illuminating light. In certain instances, the light source is a single wavelength laser, such as a single wavelength diode laser (e.g., a 488 nm laser). In some embodiments, the subject systems include a single light source (e.g., a laser). In other embodiments, the subject systems include two or more different light sources, such as 3 or more different light sources, such as 4 or more different light sources and including 5 or more different light sources. For example, systems may include a first light source (e.g., laser) outputting a first wavelength and a second light source outputting a second wavelength. In other embodiments, systems include a first light source outputting a first wavelength, a second light source outputting a second wavelength and a third light source outputting a third wavelength.

Each light source may have a wavelength which ranges from 300 nm to 1000 nm, such as from 350 nm to 950 nm, such as from 400 nm to 900 nm and including from 450 nm to 850 nm. In certain embodiments, the light source has a wavelength that corresponds to an absorption maximum of one or more fluorophores (as described below). For example, the light source may output light having a wavelength that is in the range of one or more of 280-310 nm, 305-325 nm, 320-350 nm, 340-375 nm, 370-425 nm, 400-450 nm, 440-500 nm, 475-550 nm, 525-625 nm, 625-675 nm and 650-750 nm. In certain embodiments, each light source outputs light having a wavelength that is selected from 348 nm, 355 nm, 405 nm, 407 nm, 445 nm, 488 nm, 640 nm and 652 nm.

The system 10 includes a laser radiation source 12 generating a laser beam 14. By way of example, the laser beam can have a frequency in a range of about 1000 THz to about 300 THz, corresponding to a vacuum wavelength in a range of about 300 nm to about 1000 nm. The beam diameter of the laser beam (e.g., the beam waist when a Gaussian laser beam is employed) can be, for example, in a range of about 0.1 mm to about 10 mm. Without any loss of generality, in this embodiment the laser 12 emits radiation at a wavelength of 488 nm with a beam diameter of about 1 mm.

The frequency of the laser beam can be selected based on a particular application(s) for which the system is intended. Specifically, as discussed in more detail below, the laser frequency can be suitable for exciting an electronic transition of a fluorophore of interest, e.g., via absorption of the radiation, so as to cause the fluorophore to emit fluorescence radiation at a lower frequency. A variety of laser sources can be employed. Some examples of such laser sources include, without limitation, Sapphire 488-SF, marketed by Coherent, Inc. of Santa Clara, Calif. U.S.A., Genesis MX-488-1000-STM (Coherent, Inc.), OBIS 405-LX (Coherent, Inc.), Stadus 405-250 marketed by Vortran Laser Technology, Inc. of Sacramento, Calif. U.S.A., and LQC-660-110 of Newport Corporation of Irvine, Calif. U.S.A. Without any loss of generality, in the present embodiment the laser beam is assumed to have a Gaussian intensity profile in a plane perpendicular to its propagation direction.

A mirror 16 receives the laser radiation beam 14 and directs the laser beam via reflection to an acousto-optic deflector (AOD) 18. In this embodiment, the AOD 18 is mounted on an adjustable post holder mount (A) that allows rotation of the AOD about an axis perpendicular the propagation direction of the beam 14. A direct digital synthesizer (DDS) 20 operating under control of a controller 21 can apply one or more drive signals to the AOD 18. By way of example, in some embodiments, these drive signals can span a frequency range of about 50 MHz to about 250 MHz. For example, the drive signals applied to the AOD may from 55 MHz to 225 MHz, such as from 60 MHz to 200 MHz, such as from 65 MHz to 175 MHz, such as from 70 MHz to 150 MHz and including from 75 MHz to 125 MHz. In some embodiments, the drive signals may be separated from one another by a frequency in a range of about 0.1 MHz to about 4 MHz. For example, the drive signals may be separated from one another by a frequency of from about 0.2 MHz to about 3.9 MHz, such as from about 0.3 MHz to about 3.8 MHz, such as from about 0.4 MHz to about 3.7 MHz, such as from about 0.5 MHz to about 3.6 MHz and including from about 1 MHz to about 3.5 MHz. In this embodiment, an electronic power amplifier 21' amplifies the radiofrequency signals generated by the DDS 20 for application to the AOD 18.

In the operational mode in which a sample is illuminated concurrently with a plurality of excitation frequencies, the RF comb generator 20 applies a plurality of RF drive signals concurrently to the AOD 18. By way of example, the number of simultaneously applied RF drive signals can be in a range of about 20 to about 200. The interaction of the laser beam and the drive signals results in generation of a plurality of angularly separated laser beams each having a frequency shift corresponding to one of the drive signals relative to the frequency of the laser beam generated by the laser 12. Without being limited to any particular theory, in an AOD, a piezoelectric transducer can generate radiofrequency phonons in a crystal, e.g., a quartz crystal, and the scattering of the optical photons of the laser beam by such radiofrequency phonons can result in the generation of the frequency-shifted laser beams. One of these frequency-shifted beams 22 is herein referred to as a "local oscillator" (LO) beam and the remainder of the frequency shifted beams 24 are herein referred to as "RF comb beams." The angular separation of the frequency shifted beams can be, for example, in a range of about 1 milliradians to about 100 milliradians. For example, the angular separation of the frequency shifted beams may range from 2 milliradians to about 95 milliradians, such as from 3 milliradians to about 90 milliradians, such as from 4 milliradians to about 85 milliradians, such as from 5 milliradians to about 80 milliradians and including from 10 milliradians to about 75 milliradians.

The LO and the RF comb beams pass through a lens 26, which is in this embodiment a positive lens with a focal length of about 50 mm. After passage through the lens 26, the LO laser beam is intercepted by a mirror 28, which redirects the LO beam in a different direction (in this embodiment in a direction substantially orthogonal to the original propagation direction of the LO beam). The mirror 28 is positioned relative to the RF comb beams such that these beams miss the mirror 28 and propagate to a lens 30 (which in this embodiment has a focal length of 200 mm). In this manner, the LO beam and the RF comb beams are directed along different propagation directions. The use of the pickoff mirror 28 in a manner disclosed above allows utilizing a single AOD to generate both the LO beam and the RF comb beams and combining them in a manner discussed below to generate an excitation beam for illuminating a sample. The use of a single AOD, rather than multiple AODs (e.g., two AODs, one for generating the LO beam and the other for generating the RF comb beams), simplifies the design of the system and further allows efficient use of the system in multiple distinct operational modes, as discussed in more detail below.

In some embodiments, the beam profile of the LO beam is modified before recombining with the RF comb beams. For example, the beam profile of the LO beam may be adjusted (increased or decreased) in spatial dimension, beam shape, intensity, spatial distribution of beam, or any combination thereof. In certain embodiments, the spatial dimensions of the beam profile of the LO beam are modified. For example, the beam profile may be adjusted to elongate the beam profile in one or more dimensions, such as along an axis that is orthogonal to the longitudinal axis of a flow stream. In one example according to these embodiments, the spatial dimension (e.g., in one or more dimensions) of the beam profile may be increased by 1% or more, such as by 2% or more, such as by 3% or more, such as by 5% or more, such as by 10% or more, such as by 25% or more, such as by 50% or more, such as by 75% or more, such as 90% or more, such as by 1.5-times or more, such as by 2-times or more, such as by 3-times or more and including by 5-times or more. In another example according to these embodiments, the spatial dimension (e.g., in one or more dimensions) of the beam profile may be decreased by 1% or more, such as by 2% or more, such as by 3% or more, such as by 5% or more, such as by 10% or more, such as by 25% or more, such as by 50% or more, such as by 75% or more, such as 90% or more, such as by 1.5-times or more, such as by 2-times or more, such as by 3-times or more and including by 5-times or more.

In other embodiments, the beam shape of the LO beam is modified. For example, the beam shape may be modified to elongate the beam profile in one or more dimensions. In certain instances, the beam shape of the LO beam is elongated in a plane perpendicular to the propagation of the direction of the LO beam. In certain embodiments, the shape of the LO beam profile is changed from a circular beam profile to an oval beam profile that is elongated in an axis orthogonal to the longitudinal axis of the flow stream. In other embodiments, the shape of the LO beam profile is changed from a circular beam profile to a rectangular beam profile that has a long dimension in an axis orthogonal to the longitudinal axis of the flow stream.

In still other embodiments, the intensity of the LO beam is modified. For example, the intensity of the LO beam may be increased, such as by 1% or more, such as by 2% or more, such as by 3% or more, such as by 5% or more, such as by 10% or more, such as by 25% or more, such as by 50% or more, such as by 75% or more, such as 90% or more, such as by 1.5-times or more, such as by 2-times or more, such as by 3-times or more and including by 5-times or more. In other embodiments, the intensity of the LO beam is decreased, such as by 1% or more, such as by 2% or more, such as by 3% or more, such as by 5% or more, such as by 10% or more, such as by 25% or more, such as by 50% or more, such as by 75% or more, such as 90% or more, such as by 1.5-times or more, such as by 2-times or more, such as by 3-times or more and including by 5-times or more. In certain embodiments, the intensity of the LO beam is modified to match the intensity of the RF comb beams. For example, the LO beam may have an intensity that differs from the intensity of the RF comb beams by 10% or less, such as by 9% or less, such as by 8% or less, such as by 7% or less, such as by 6% or less, such as by 5% or less, such as by 4% or less, such as by 3% or less, such as by 2% or less, such as by 1% or less, such as by 0.01% or less and including where the intensity of the LO beam differs from the RF comb beams by 0.001% or less. In certain instances, the intensities of the LO beam and the RF comb beams are identical.

In yet other embodiments, the spatial distribution of the beam profile may also be modified. For example, the LO beam may be modified such that the intensity of the LO beam is no longer Gaussian in one or more dimensions. For example, the LO beam may be modified to have a Gaussian distribution along a first axis that is parallel to the longitudinal axis of the flow stream and non-Gaussian along a second axis that is orthogonal to the longitudinal axis of the flow stream.

Any beam shaping protocol may be employed to modify the beam profile of the LO beam, including but not limited to refractive and diffractive beam shaping protocols. In some embodiments, the LO beam is modified by a top-hat beam shaper.

In this embodiment, the LO beam propagates to another positive lens 32 (which in this embodiment has a focal length of about 200 mm). The combination of the lens 26 and the lens 32 magnifies and collimates the LO beam in order to appropriately fill the back aperture of a top-hat beam shaper 34. More specifically, the LO beam 22 passes through the lens 32 and is reflected by mirrors 33 and 35 to the top-hat beam shaper 34.

The top-hat beam shaper 34 shapes the phase front of the Gaussian LO beam to enable formation of a top-hat intensity profile. More specifically, the LO laser beam 22' exiting the top-hat beam shaper is reflected by a beam splitter 44 and is focused by lens 46 (which in this embodiment has a focal length of 100 mm) onto an intermediate image plane 48. The laser beam on the intermediate image plane 48 has a top-hat intensity profile along a horizontal direction in a plane perpendicular to the propagation direction of the beam. Similar to the AOD 18, in this embodiment, the beam splitter 44 is mounted on an adjustable post holder mount (B). In this embodiment, the top-hat beam shaper generates a top-hat beam profile in which the polarization of radiation is substantially uniform along the top-hat direction of the beam (along the horizontal direction in this embodiment).

Figure 2A:
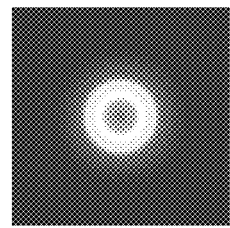
FIG. 2A is a schematic, exemplary profile of a Gaussian beam in a plane perpendicular to the beam's propagation direction.
Figure 2B:
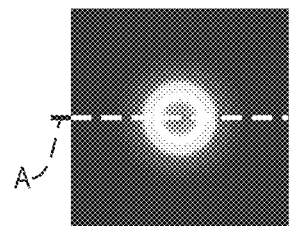
FIG. 2B is a schematic, top-hat beam profile obtained by passing the Gaussian beam shown in FIG. 2A through a top-hat beam shaper and focusing the output beam of the beam shaper, FIG. 3 schematically depicts components of an exemplary top-hat beam shaper, FIG. 4 schematically depicts cross-sectional beam profiles of a plurality of RF comb beams, FIG. 5 schematically depicts superposition of the RF comb beams depicted in FIG. 4 and an LO beam having a top-hat beam profile, FIG. 6 schematically depicts the combined beam shown in FIG. 5 illuminating a sample under analysis, FIG. 7 schematically depicts exemplary energy levels of a hypothetical fluorophore, FIG. 8 schematically depicts an absorption curve corresponding to the hypothetical fluorophore of FIG. 7, FIG. 9A schematically depicts a detection system according to an embodiment of the present teachings, which includes an optical fiber for transmission of fluorescence radiation, FIG. 9B schematically depicts another detection system according to an embodiment of the present teachings in which fluorescence radiation propagates through free space to reach a plurality of photodetectors, FIG. 9C schematically depicts a brightfield and a darkfield image generation arms for use in some embodiments of the present teachings, FIG. 9D schematically depicts a detection system for use in some embodiments of the present teachings, which includes a detection arm for generating a brightfield image and a detection arm which integrates the capabilities for the detection of excitation radiation scattered from a sample as well as fluorescence radiation emitted by the sample, FIG. 10 schematically depicts that a fluorescence signal generated by a photodetector in an embodiment of a system according to the present invention can be amplified by an amplifier and the amplified signal can be analyzed by an analysis module to construct a fluorescence image of a sample under analysis.

By way of illustration, FIG. 2A schematically depicts the Gaussian intensity profile of the LO laser beam as it enters the top-hat beam shaper. As shown schematically in FIG. 2B, on the intermediate image plane 48, the LO laser beam exhibits a beam profile that is stretched in the horizontal direction (in a direction perpendicular to the page in this illustration) and is substantially constant along each horizontal line extending through the profile, e.g., the horizontal line A, but varies vertically according to a Gaussian profile.

Figure 3:
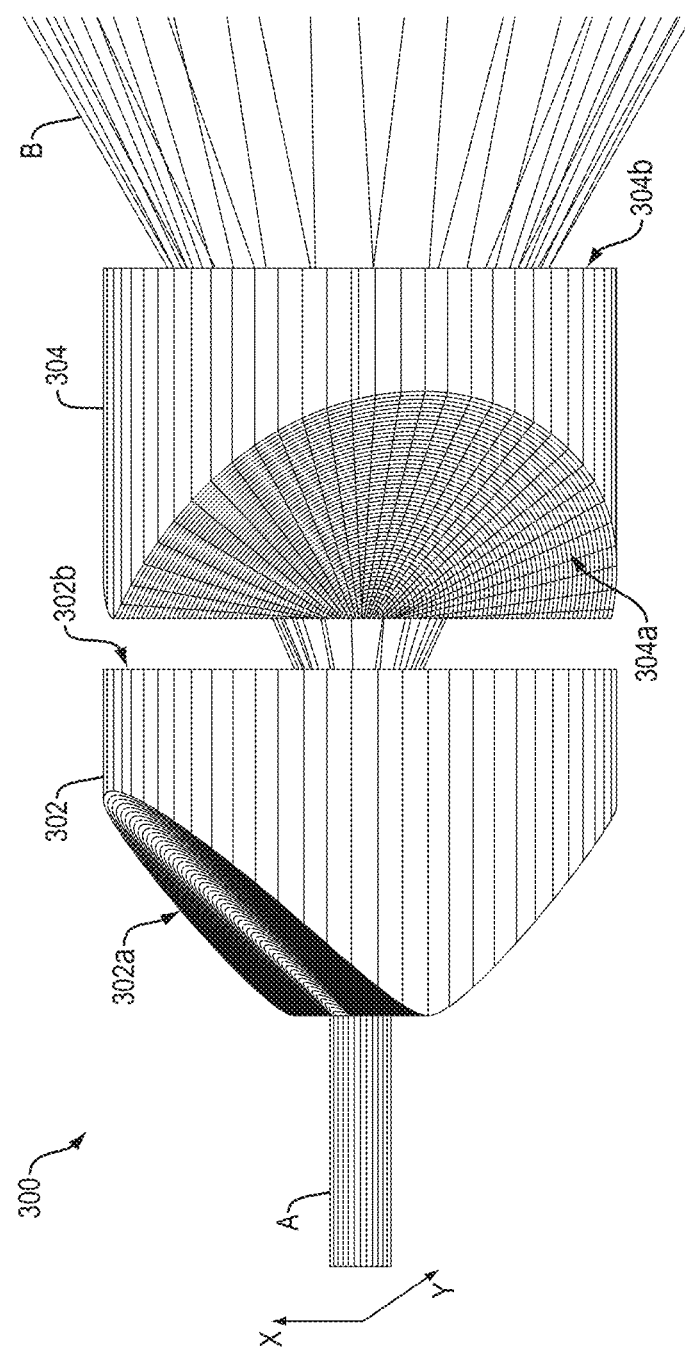

A variety of top-hat beam shapers can be employed. By way of example, refractive optical elements having an aspherical surface or diffractive optical elements can be used to produce beams with appropriate spatial phase fronts, which, after focusing by a lens, will produce a top hat profile pattern at the focal plane of the lens. Multiple form factors exist for such top-hat beam shapers, and a variety of implementations of this approach are available to create the appropriate LO beam shape at the sample in various embodiments of the present teachings. For example, U.S. Pat. No. 6,295,168 entitled "Refractive optical system that converts a laser beam to a collimated flat-top beam" and U.S. Pat. No. 7,400,457 entitled "Rectangular flat-top beam shaper," both of which are herein incorporated by reference in their entirety, disclose beam shaping systems that can be employed as the flat-top beam shaper in a system according to some embodiments of the present teachings. By way of illustration, FIG. 3 is a reproduction of FIG. 1 of U.S. Pat. No. 7,400,457 (with different reference numerals) that schematically depict a beam shaping system 300 for providing a square or a rectangular beam, which includes two orthogonally disposed acylindrical lenses 302 and 304. The first acylindrical lens 302 is for shaping an incident beam A along the X-axis and the second acylindrical lens 304 for shaping the incident beam A along the Y-axis. The two crossed acylindrical lenses are adapted to provide a resulting rectangular laser beam B having a flat-top profile along the X-axis. The input surface 302a of the acylindrical lens 302 is a convex acylindrical surface having a variable radius of curvature that is smaller in the center of the surface and increases smoothly toward both extremities of the lens. The second acylindrical lens 304 is similar to the first acylindrical lens but is orthogonally disposed relative to the lens 302 in order to shape the beam along the Y-axis. The profiles of input surfaces 302a/304a, and output surfaces 302b/304b of the lenses 302 and 304 can be independently selected as a function of the X and Y-profiles of the indicent beam A and the desired intensity profile of the resultant rectangular beam B (See, e.g., columns 5 and 6 of the patent).

An example of a commercially available top-hat beam shaper that can be employed includes, for example, DTH-1D-0.46 deg-4 mm marketed by Osela, Inc. of Lachine, Canada.

As discussed in more detail below, the use of a beam shaper to stretch the LO beam along the horizontal direction provides a number of advantages. For example, it can ensure that the combination of the LO beam and the RF comb beams illuminates a plurality of sample locations with a substantially similar illumination intensity, in order to match the intensities of the LO and RF comb beams across the entirety of the sample locations, thereby creating an intensity amplitude modulation of the fluorescence signal with high modulation depth. In absence of such intensity matching, the imaging system may have a small view and may not utilize all of the frequencies (pixels) driving the AOD. As the modulation depth of the fluorescence signal plays an important role in the ability of the system to reconstruct a fluorescence image of the sample, a uniformly-high modulation depth of the excitation beat frequencies at all pixels is particularly advantageous to the operation of the system. Further, the amplitudes of electronic signals applied to the AOD for generating the RF comb beams can be adjusted by controlling the output of the direct digital synthesizer (e.g., by employing the controller 21) in order to equalize the RF comb beams such that their intensities are equal to that of the LO beam across all spatial locations in which the RF comb beams and the LO beam overlap. This feature provides an advantage in that it ensures high modulation depth of the intensity amplitude modulation of the fluorescence radiation.

Referring again to FIG. 1, the RF comb beams 24 are imaged via the combination of the lenses 26 and 30 onto an intermediate image plane 38. More specifically, the RF comb beams 24 pass through the lens 26 and miss the mirror 28 to reach the lens 30, which directs the RF comb beams via mirrors 40 and 42 to the intermediate image plane 38.

Figure 4:
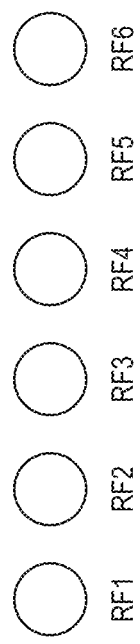

FIG. 4 schematically depicts the distribution of an exemplary number of RF comb beams in the intermediate image plane 38 (without loss of generality, the number of RF comb beams is selected to be 6 for illustration purposes (labeled as RF1, . . . , RF6), though other numbers can also be employed). As shown in FIG. 4, in the intermediate image plane 38, the RF comb beams 24 are spatially separated from one another along the horizontal direction. In other embodiments, two or more of the RF comb beams 24 may partially overlap. Thus, the combination of the lenses 26 and 30 transform the angularly separated RF comb beams into a set of spatially separated beams that span over a horizontal extent.

Referring again to FIG. 1, as discussed above, the beam splitter 44 receives the laser beam 22' exiting the top-hat beam shaper 34 and reflects that beam to lens 46, which in turn focuses the beam on the intermediate image plane 48 in which the LO beam exhibits a top-hat beam profile. The beam splitter also receives the RF comb beams 24 from the intermediate image plane 38 and allows the passage of the RF comb beams therethrough. The lens 46 focuses the RF comb beams 24 onto the intermediate image plane 48 to be combined with the LO beam having a top-hat beam profile to generate a combined beam 49.

Figure 5:
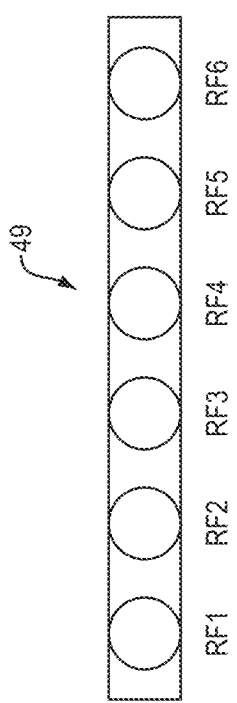

By way of illustration, FIG. 5 schematically depicts one exemplary profile of the combined beam 49 in a plane perpendicular to its propagation axis. The intensity profile of the combined beam is generated as a superposition of the intensity profile of the top-hat LO beam (shown schematically by the square) and those of the RF comb beams 24 (each shown schematically by one of the circles). As discussed in more detail below, this superposition of the LO beam and the RF comb beams provides, along a horizontal extent, a plurality of beat frequencies each corresponding to one spatial location along that horizontal extent. Upon illuminating a horizontal extent of a sample, the fluorescence radiation emitted from a location of the sample encodes, via amplitude modulation, the beat frequency associated with radiation illuminating that location.

Referring again to FIG. 1, a positive lens 50 (200-mm lens in this embodiment) and an objective lens 52, mounted in this embodiment on an adjustable post holder mount C, form a telescope for relaying the image at the intermediate plane 48 onto a sample flowing through a flow cell 54. In this embodiment, a mirror 56 reflects the combined beam 49 to the lens 50, and a dichroic mirror 58 reflects the combined light beam after its passage through the lens 50 toward the objective lens 52.

As shown schematically in FIG. 6, the combined beam 49 concurrently illuminates a plurality of spatial locations 60 of a sample 62 flowing through the flow cell 54. Thus, each location 60 is illuminated by the overlap of one of the RF comb beams with a portion of the top-hat shaped LO laser beam. At these spatial locations, the radiation will excite a fluorophore of interest in the sample, if present. More specifically, in this embodiment, the LO beam and the RF comb beams excite concurrently the fluorophore, e.g., via causing electronic transition thereof to an excited electronic state, at a plurality of sample locations 60.

In some embodiments, the sample can include a flowing fluid, in which a plurality of cells are entrained. In some cases, the cells can be labeled with one or more fluorescent markers (fluorophores). Some examples of fluorescent markers include, without limitation, fluorescent proteins (e.g., GFP, YFP, RFP), antibodies labeled with fluorophores (e.g., fluorescein isothiocyanate) (FITC), phycoerythrin (PE), allophycocyanin (APC)), nucleic acid stains (e.g., 4',6-diamidino-2-phenylindole (DAPI), SYTO16, propidium iodide (PI)), cell membrane stains (e.g., FMI-43), and cell function dyes (e.g., Fluo-4, Indo-1). In other cases, endogenous fluorophores present in cells can be employed to elicit fluorescent radiation from the cells. As discussed in more detail below, such exogenous or endogenous fluorophores undergo electronic excitation in response to the illuminating radiation and emit fluorescent radiation (typically at a lower frequency than the excitation frequency), which is collected and analyzed.

By way of illustration and without being limited to any particular theory, FIG. 7 shows hypothetical energy levels corresponding to a ground electronic state A as well as two electronic excited electronic states B and C of a fluorophore. The fluorophore can be excited from its ground electronic state (A) to the excited electronic state (B) via absorption of radiation energy. The fluorophore can then relax into the lower excited state B, e.g., via a radiation-less transition mediated by vibrational modes of the fluorophore. The fluorophore can further relax from the lower electronic state C to the ground state, via an optical transition, thereby emitting fluorescence radiation at a frequency less than that of the excitation frequency. It should be understood that this hypothetical example is provided only for illustration purposes, and not to indicate the only mechanism by which fluorescence radiation can be emitted.

In many cases, the fluorophore can absorb electromagnetic radiation over a range of frequencies to be excited from the ground state to the excited electronic state. By way of illustration, FIG. 8 shows an absorption curve for the hypothetical fluorophore discussed in connection with FIG. 7. In one implementation of an embodiment according to the present teachings the LO frequency can be selected to coincide with the frequency corresponding to the peak absorption of a fluorophore of interest. The radiofrequency-shifted beams can have frequencies separated from the peak absorption by their respective beat frequencies. Typically, these frequency separations are small in comparison to the absorption bandwidth of the fluorophore so as to avoid any degradation of the excitation frequency. By way of example and only by way of illustration, the dashed lines A and B schematically depict the frequency of the LO beam and one of the RF comb beams (the figures is not drawn to scale for ease of description). The concurrent illumination of a spatial location of the sample by both the LO laser beam and one of the depicted RF comb beams results in fluorescence radiation exhibiting an amplitude modulation at a beat frequency corresponding to a difference between the LO and the RF comb beam frequencies.

Again by way of illustration and without being limited to any particular theory, the electric field applied to the fluorophore via its concurrent illumination by the LO beam and one of the RF comb beams can be mathematically defined as follows:

$$E_{com} = E_{RF} e^{j(\omega_0 + \omega_{RF})} + E_{LO} e^{j(\omega_0 + \omega_{LO})} \quad \text{Eq. (1)}$$

wherein, $E_{com}$ denotes the electric field of the combined beam, $E_{RF}$ denotes the amplitude of the electric field associated with one of the RF comb beams, $E_{LO}$ denotes the amplitude of the electric field associated with the LO beam, $\varphi_0$ denotes the frequency of the laser beam generated by the laser 12, $\varphi_{RF}$ denotes the frequency shift associated with the RF comb beam, and $\varphi_{LO}$ denotes the frequency shift associated with the LO beam.

The intensity of the fluorescence radiation emitted in response to the superposition of the electric fields of the LO and RF comb beams would exhibit a modulation at a beat frequency corresponding to ($\omega_{RF}-\omega_{LO}$). Hence, the fluorescence radiation emanating from each spatial location of the sample illuminated by superposition of the LO beam and one of the RF comb beams exhibits a modulation at a beat frequency corresponding to the difference between the radiofrequency shift associated with the LO beam and that associated with the RF comb beam illuminating that spatial location.

As the process of fluorescence emission requires a finite amount of time (typically 1-10 nanoseconds for common organic fluorophores), the emitted fluorescence will not exhibit a high modulation depth if the excitation beat frequency is too high. Thus, in many embodiments, the excitation beat frequencies are selected to be considerably less than $1/\tau_f$, where $\tau_f$ is the characteristic fluorescence lifetime of the fluorophore. In some instances, the excitation beat frequencies may be less than $1/\tau_f$ by 1% or more, such as by 1% or more, such as by 2% or more, such as by 3% or more, such as by 5% or more, such as by 10% or more, such as by 25% or more, such as by 50% or more, such as by 75% or more, such as 90% or more, such as by 1.5-times or more, such as by 2-times or more, such as by 3-times or more and including by 5-times or more. For example, the excitation beat frequencies may be less than $1/\tau_f$ by 0.01 MHz or more, such as by 0.05 MHz or more, such as by 0.1 MHz or more, such as by 0.5 MHz or more, such as by 1 MHz or more, such as by 5 MHz or more, such as by 10 MHz or more, such as by 25 MHz or more, such as by 50 MHz or more, such as by 100 MHz or more, such as by 250 MHz or more, such as by 500 MHz or more and including by 750 MHz or more.

In embodiments, the photodetector is configured to detect light (e.g., luminescence such as fluorescence) from the irradiated sample. In embodiments, the photodetector may include one or more detectors, such as 2 or more detectors, such as 3 or more detectors, such as 4 or more detectors, such as 5 or more detectors, such as 6 or more detectors, such as 7 or more detectors and including 8 or more detectors. Any light detecting protocol may be employed, including but not limited to active-pixel sensors (APSs), quadrant photodiodes, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In some embodiments, photodetectors of interest are configured to detect light that ranges from 350 nm to 1200 nm, such as from 450 nm to 1150 nm, such as from 500 nm to 1100 nm, such as from 550 nm to 1050 nm, such as from 500 nm to 1000 nm and including from 400 nm to 800 nm. In certain embodiments, the photodetector is configured to detect light at the emission maximum of the luminescence, such as at 395 nm, 421 nm, 445 nm, 448 nm, 452 nm, 478 nm, 480 nm, 485 nm, 491 nm, 496 nm, 500 nm, 510 nm, 515 nm, 519 nm, 520 nm, 563 nm, 570 nm, 578 nm, 602 nm, 612 nm, 650 nm, 661 nm, 667 nm, 668 nm, 678 nm, 695 nm, 702 nm, 711 nm, 719 nm, 737 nm, 785 nm, 786 nm, 805 nm.

In some embodiments, the fluorescence radiation emitted by the sample can be collected in a variety of different ways, e.g., along an optical path that is perpendicular to the propagation direction of the excitation beam. In other embodiments, the fluorescence radiation is detected in an epi-direction.

Referring again to FIG. 1, in this embodiment, the fluorescence radiation emitted by one or more fluorophores present in the illuminated sample passes through the objective lens 52 and is transmitted through the dichroic mirror 58 to reach a photodetector 64. More specifically, in this embodiment, a lens 65 focuses the fluorescent radiation transmitted through the dichroic mirror 58 onto a slit aperture 66. The fluorescent radiation that is transmitted through the slit passes through a fluorescence emission filter 68 to reach the photodetector 64. The slit aperture 66 (or an optical filter in other embodiments discussed below) disposed in front of the photodetector substantially allows the passage of the fluorescence radiation emitted from a particular plane of the sample while rejecting out-of-plane fluorescence emission. Further, the fluorescence emission filter 68, e.g., a passband filter, allows the passage of fluorescence radiation to the photodetector 64 while substantially blocking the passage of radiation at other frequencies.

The photodetector 64 has sufficient RF bandwidth to detect and transmit signals from the entire range of the beat frequencies. Some examples of suitable photodetectors include, without limitation, a photomultiplier tube, avalanche photodiode, PIN photodiode, and a hybrid photodetector, among others. By way of example, in some embodiments, a photomultiplier tube marketed by Hamamatsu Corporation can be employed (e.g., R3896, R10699, H11462). The photodetector generates a signal, e.g., an analog signal in this embodiment, in response to the detection of the received fluorescence radiation.

Figure 9A:
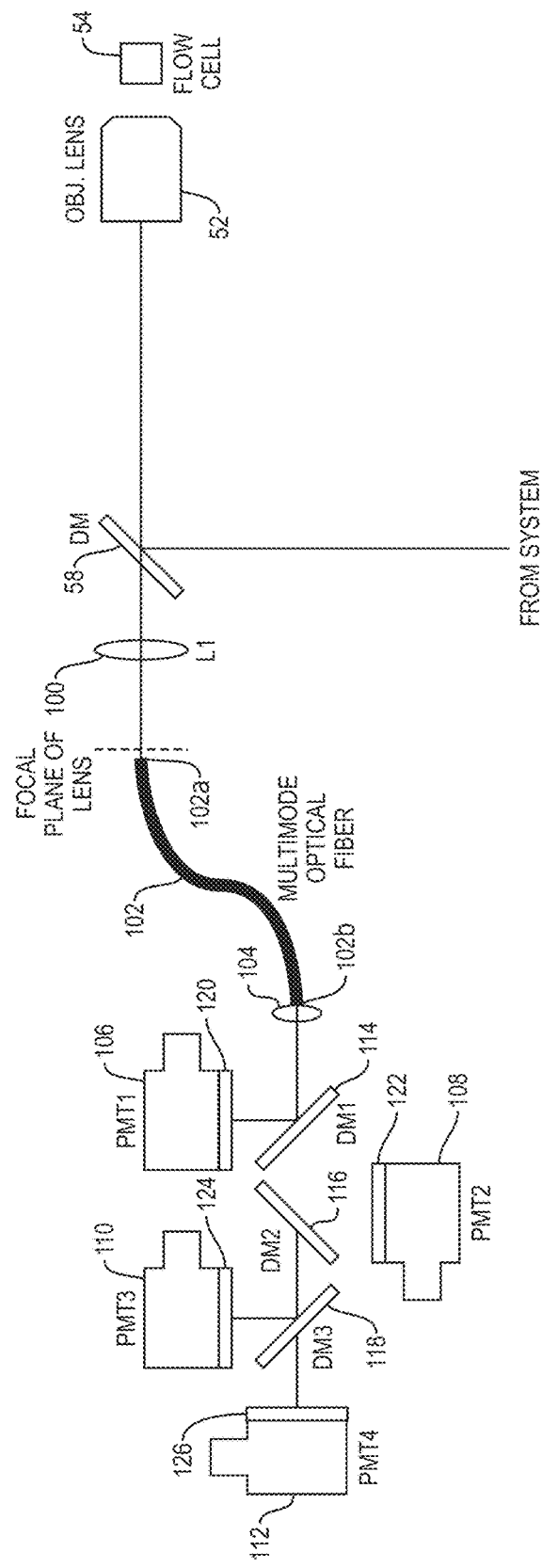

By way of another example and with reference to FIG. 9A, the fluorescence radiation emitted by the sample in response to concurrent illumination by the LO beam and the spatially separated RF comb beams passes through the objective lens 52 and the dichroic mirror 58 to be coupled via a lens 100 onto a multimode optical fiber 102, which extends from a proximal end 102a to a distal end 102b. More specifically, the proximal end 102a of the optical fiber 102 is positioned in proximity of the focal plane of the lens 100 so as to receive the fluorescent radiation. An outcoupling lens 104, coupled to the distal end 102b of the optical fiber, collimates the radiation exiting the fiber.

In many cases, the excitation radiation illuminating the sample excites multiple fluorophores (e.g., organic fluorophores) that can have broad enough radiation absorption spectra such that the excitation frequencies falls within the absorption spectra of multiple fluorophores in the sample. Each fluorophore would then emit fluorescence radiation at a different frequency. Without loss of generality and for purposes of illustration, in this embodiment, the detection system includes four photomultiplier tubes 106, 108, 110 and 112, each of which receives a portion of the collimated radiation corresponding to the fluorescence radiation emitted by one of four fluorophores excited by the excitation radiation in the illuminated sample. More specifically, a dichroic mirror 114 reflects the fluorescence radiation emitted by one of the fluorophores at a first frequency to the photomultiplier tube 106 while allowing fluorescence radiation at other frequencies to pass through. Another dichroic mirror 116 reflects the fluorescence radiation emitted by a different fluorophore at a different second frequency to the photomultiplier tube 108 while allowing the rest of the radiation containing fluorescence radiation emitted by yet another fluorophore at a third frequency to reach a third dichroic mirror 118, which reflects that fluorescence radiation to the photomultiplier tube 110. The dichroic mirror 118 allows the rest of the radiation including the fluorescence radiation emitted by a fourth fluorophore at a fourth radiation frequency to pass through to reach the photomultiplier tube 112.

A plurality of bandpass filters 120, 122, 124, and 126, each centered at one of the four fluorescence frequencies, are placed in front of the photomultiplier tubes 106, 108, 110, and 112, respectively. The signal detected by each of the photomultiplier tubes is analyzed in a manner discussed below to generate a fluorescence image at the respective fluorescence frequency. In some embodiments, rather than using multiple photodetectors, a single photodetector, e.g., a single photomultiplier tube can be used to detect fluorescence radiation, e.g., fluorescence frequency corresponding to emission from a single fluorophore.

In some embodiments, as the sample flows through the flow cell different horizontal rows of the sample are illuminated and fluorescence radiation associated with each horizontal row is detected by one or more photodetectors, such as the photomultipliers 106, 108, 110 and 112.

Figure 9B:
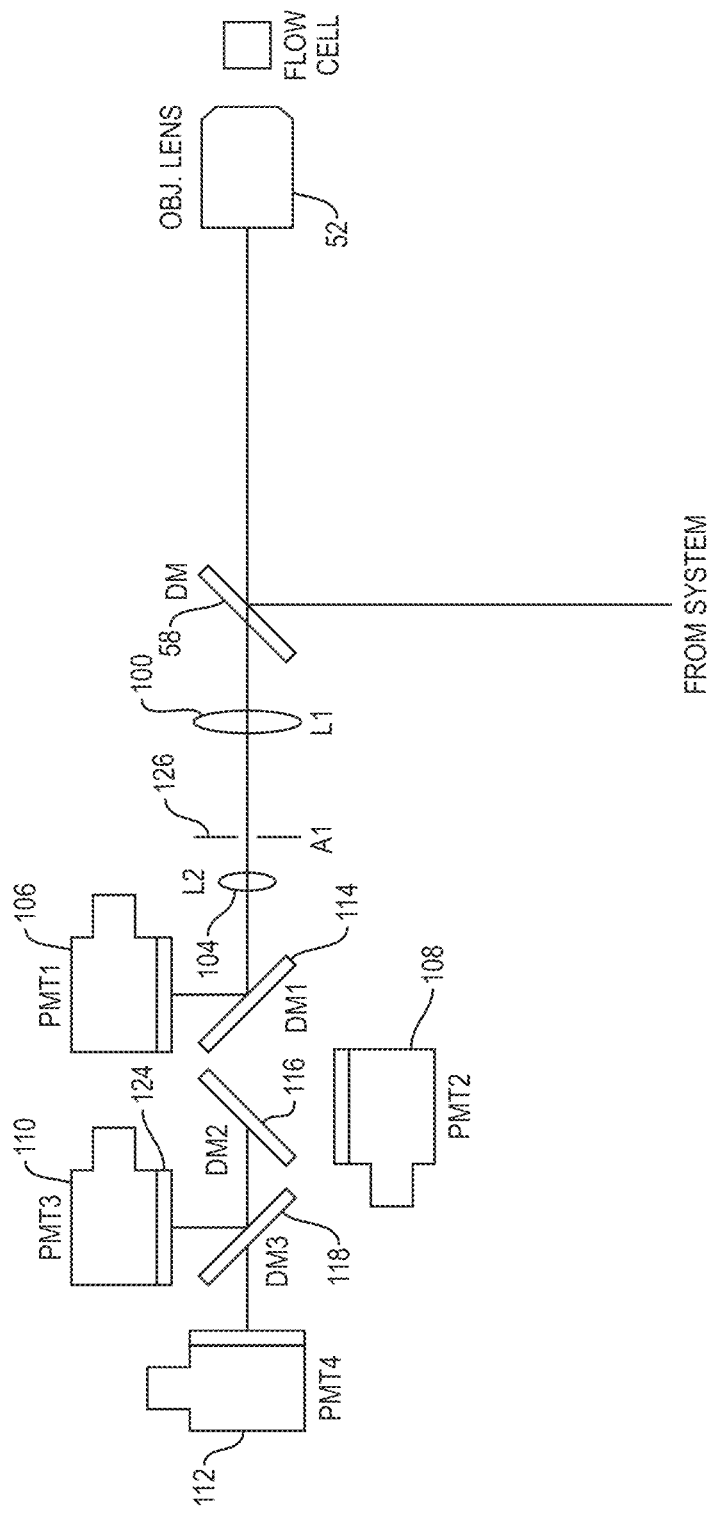

FIG. 9B schematically depicts a detection system similar to that discussed above in connection with FIG. 9A except that this detection system, rather than using an optical fiber, the fluorescence radiation containing fluorescence emission from a plurality of fluorophores passing through the dichroic mirror 58 propagates in free space to reach the photomultiplier tubes 106, 108, and 112. More specifically, the lens 100 focuses the fluorescence radiation onto an aperture 126 disposed between the lenses 100 and 104, where the aperture can reject out-of-focus radiation. The lens 104 collimates the radiation passing through the aperture, where the collimated radiation is distributed among the photomultiplier tubes in a manner discussed above in connection with FIG. 9A.

Figure 9C:
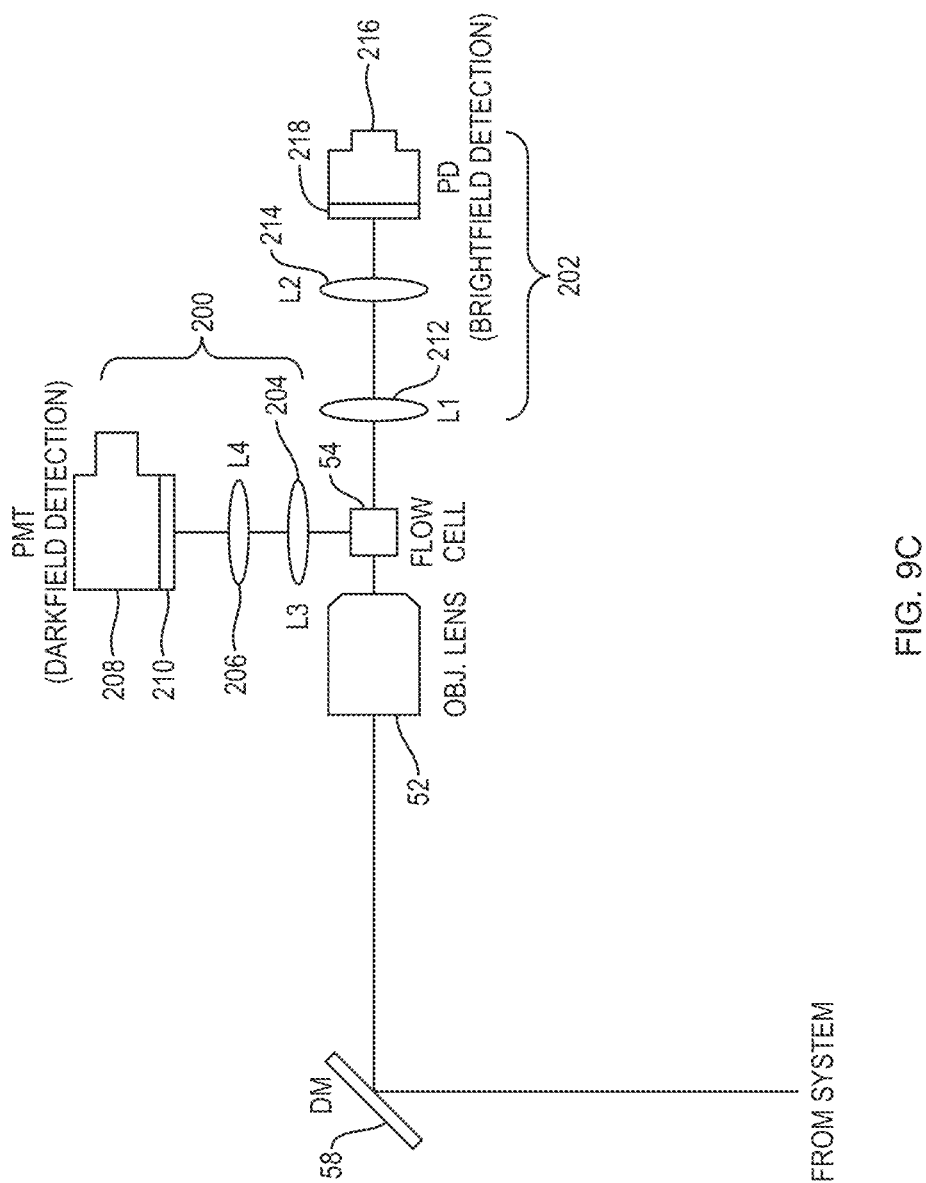

In some embodiments, the system 10 can be configured to provide a darkfield image and a brightfield image of the sample (of the flow cell in absence of the sample) using the excitation radiation. By way of example, FIG. 9C schematically depicts an embodiment of the system 10 that includes two detection arms 200 and 202 for detecting, respectively, a darkfield image and a brightfield image of the sample.

More specifically, the detection arm 200 is positioned perpendicular to the propagation of the excitation radiation so as to receive a portion of the excitation radiation that is scattered by the sample flowing through the flow cell. The detection arm 200 includes two lenses 204 and 206 that collectively direct at least a portion of the excitation radiation scattered by the sample into a solid angle subtended by the lens 204 onto a photomultiplier tube 208. More specifically, the lens 204 collimates the received scattered radiation and the lens 206 focuses the collimated scattered radiation onto the photomultiplier tube 208. In this embodiment, an appropriate bandpass filter 210 is disposed in front of the photomultiplier tube 208 to allow the passage of radiation having the desired frequency to the photomultiplier tube 208 while blocking radiation at unwanted frequencies. The output of the photomultiplier tube 208 can be processed in a manner known in the art, e.g., by an analysis module such as that discussed below to generate a darkfield image.

The detection arm 202 in turn includes two lenses 212 and 214, where the lens 212 collimates the excitation radiation exiting the flow cell in a forward direction (substantially along the propagation direction of the excitation radiation entering the flow cell 54) and the lens 214 focuses the collimated radiation onto a photodetector 216. An appropriate filter 218, e.g., a bandpass filter, disposed in front of the photodetector allows transmission of the excitation frequencies to the photodetector 216 while substantially blocking other radiation frequencies. The output of the photodetector 216 can be processed in a manner known in the art to generate a brightfield image of the flow cell.

Thus, the detection arm 200 detects the excitation radiation that is scattered by the fluid flowing through the cell, and the detection arm 202 detects the excitation radiation that is transmitted through the flow cell. When no fluid is flowing through the flow cell, the signal detected by the photomultiplier tube 208 is low and the signal detected by the photodetector 216 is high as there is little scattering of the excitation radiation passing through the flow cell and hence a large percentage, and in some cases all, of the excitation radiation is transmitted through the flow cell. In contrast, the flow of a fluid sample through the flow cell can cause the signal generated by the photomultiplier tube 208 to increase due to scattering of a portion of the excitation radiation by the sample, and the signal generated by the photodetector 216 decreases as the level of the excitation radiation transmitted through the flow cell decreases.

Figure 9D:
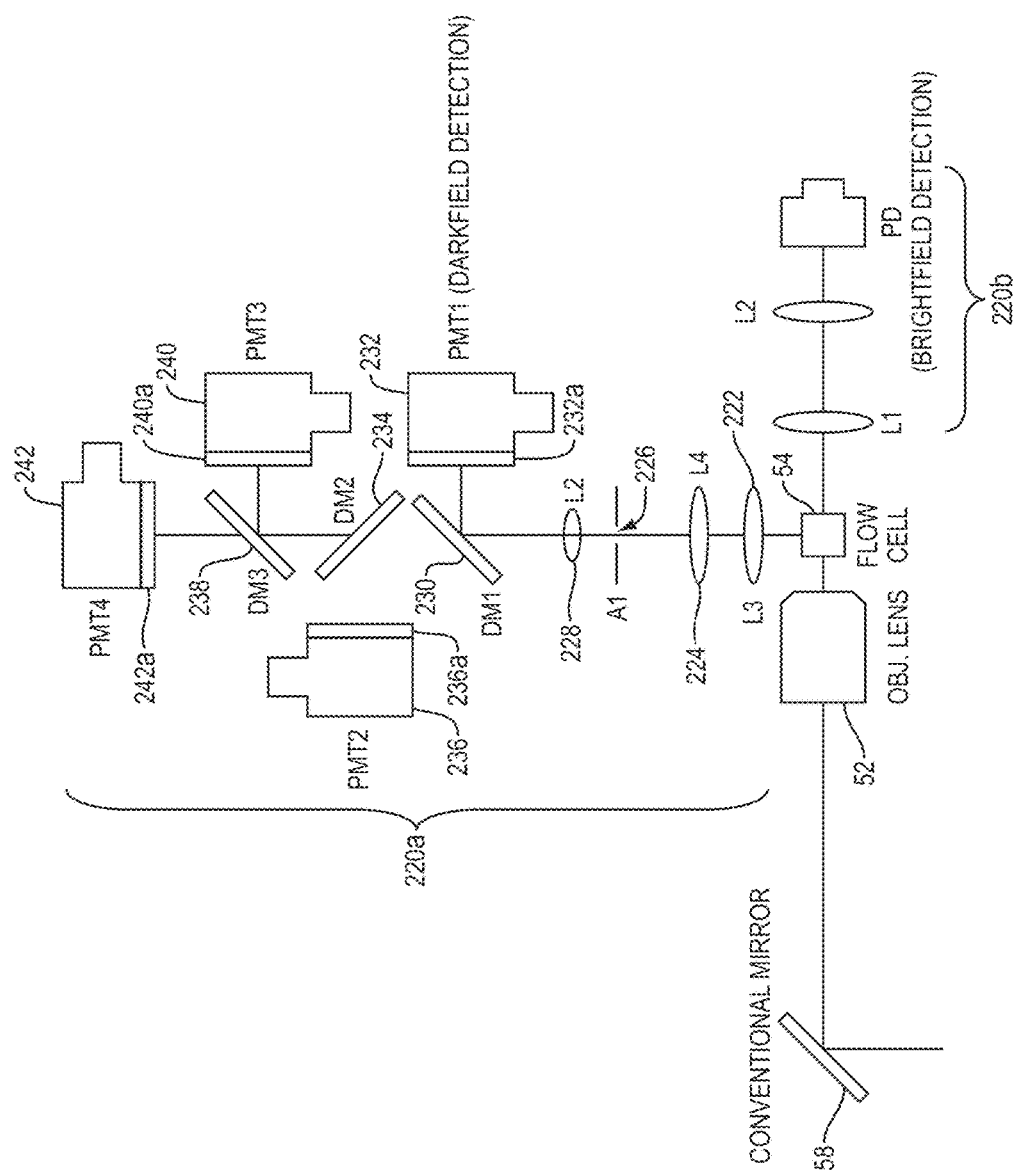

By way of further example and with reference to FIG. 9D, in one embodiment of a system according to the present teachings, a detection arm 220a positioned relative to the flow cell 54 in a direction substantially orthogonal to the propagation direction of the excitation radiation includes photodetectors for detecting both the fluorescence radiation emitted by a plurality of fluorophores in the sample as well as excitation radiation that is scattered by the sample. More specifically, the detection arm 220 includes lenses 222 and 224 that direct the fluorescence radiation as well as the scattered excitation radiation onto an aperture 226, which rejects unfocused radiation. A lens 228 collimates the radiation passing through the aperture. A dichroic mirror 230 reflects the portion of the radiation at the excitation frequencies onto a photomultiplier tube 232 for detection of a darkfield image while allowing fluorescence radiation to pass through. An appropriate filter 232a, e.g., a bandpass filter, disposed in front of the photomultiplier tube 232 allows the passage of radiation at excitation frequencies to the photomultiplier tube 232 while blocking unwanted radiation frequencies. Another dichroic mirror 234 reflects fluorescence radiation emitted by a fluorophore at a first frequency onto a photomultiplier tube 236 while allowing the passage of fluorescence radiation emitted by other fluorophores at other frequencies. Another dichroic mirror 238 reflects fluorescence radiation emitted by another fluorophore at a second frequency onto a photomultiplier tube 240 while allowing the passage of fluorescence radiation emitted by yet another fluorophore at a third frequency, where it is detected by the photomultiplier tube 242. Similar to the previous embodiments, a plurality of filters 236a, 240a, and 242a are disposed in front of the photomultiplier tubes 236, 240, and 242, respectively, to allow the transmission of radiation at desired frequencies while substantially blocking unwanted radiation frequencies.

With continued reference to FIG. 9D, this implementation of a system according to the present teachings further includes another detection arm 220b for generating a brightfield image, e.g., in a manner discussed in connection with FIG. 9C. More specifically, the detection arm 202 includes two lenses 212 and 214 that focus the light onto a photodetector 216 for generating a brightfield image of the excitation radiation. A filter 218, e.g., a bandpass filter, is placed in front of the photodetector 216 to allow the passage of the excitation radiation to the detector while rejecting unwanted radiation frequencies.

Figure 10:
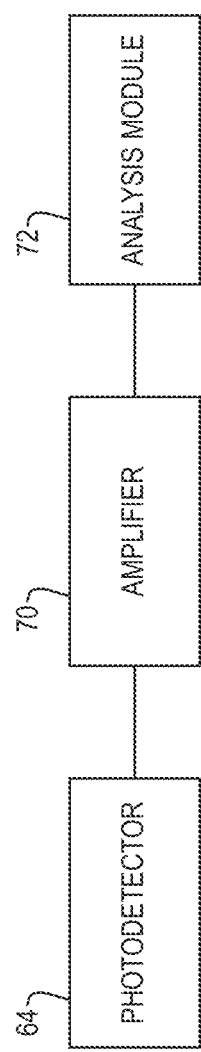

Referring again to FIG. 1 as well as FIG. 10, in this embodiment, a transimpedance amplifier 70 can be coupled to the output of photodetector 64 (or each of the photodetectors discussed in connection with FIGS. 9A-9D) to amplify the signal generated by the photodetector. A data analysis unit 72 (herein also referred to as an analysis module or an analyzer) receives the amplified signal and analyzes the signal to generate a fluorescence image of the sample. The data analysis unit 72 can be implemented in hardware, firmware, and/or software. By of example, a method for analyzing the detected fluorescence data can be stored in a read-only-memory (ROM) unit of the analysis module to be accessed under the control of a processor to analyze the received fluorescence signal.

As discussed in more detail below, the analysis method determines the frequency components of the time-varying photodetector's output and constructs a fluorescence image of the sample based on those frequency components. A variety of methods for determining the frequency content of the photodetector's output can be employed. Some examples of such suitable methods include, without limitation, Fourier transform, lock-in detection, filtering, I/Q demodulation, homodyne detection, and heterodyne detection.

Figure 11A:
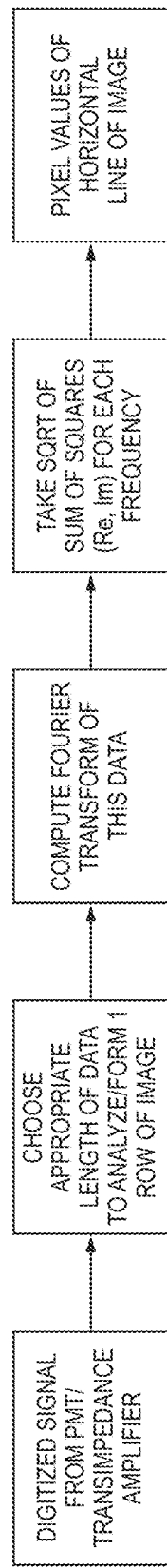
FIGS. 11A and 11B depict various steps in a method according to an embodiment of the present invention for analysis of fluorescence signal obtained by illuminating a sample with a combined beam composed of a plurality of RF comb beams and a top-hat profiled LO beam, FIG. 12 schematically depicts selected components of an exemplary hardware implementation of an analysis module according to an embodiment of the present invention.
Figure 11B:
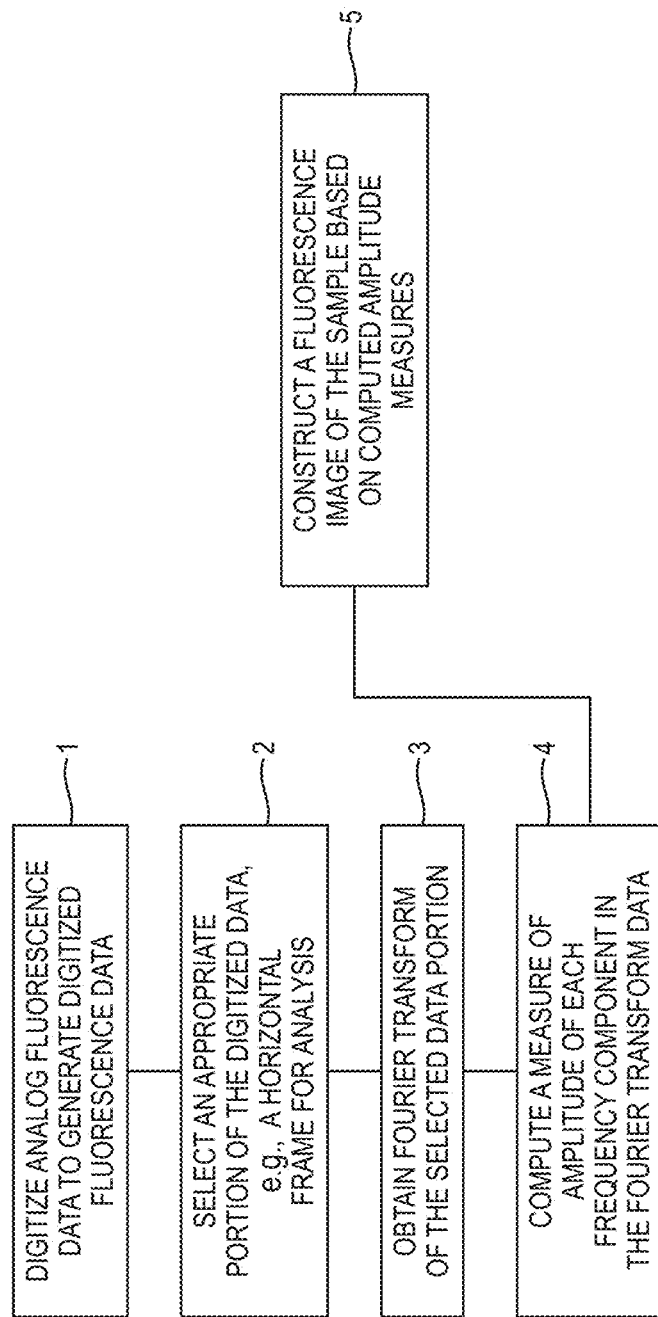

By way of example, FIGS. 11A and 11B show exemplary analysis steps that can be performed by the analysis module 72 to generate a fluorescence image of the sample. In step (1), the analog amplified signal is digitized to generate digitized fluorescence data. In step (2), an appropriate portion (length) of the digitized data is selected for analysis. For example, the fluorescence data corresponding to an illuminated row of the sample (herein also referred to as a frame) can be chosen for analysis. Alternatively, a portion of a data frame can be selected for analysis.

In step (3), a Fourier transform of the selected data is performed. By way of example, in some embodiments, a Fast Fourier Transform (FFT) of the data is performed to determine frequency components of the data. In some such embodiments, the bins of the FFT can correspond to the frequencies chosen for data acquisition. For example, for a 256 MHz sampling rate, 256 samples can yield frequency bins that are separated from one another by 1 MHz, e.g., from DC to 128 MHz. The FFT analysis provides frequencies corresponding to the beat frequencies at which the emitted fluorescence emission exhibits amplitude modulation.

With continued reference to FIGS. 11A and 11B, in this embodiment, in step (4), a measure of the amplitude of each frequency component present in the FFT data is computed by obtaining the square root of the sum of squares of the real and imaginary components of that frequency component. As each frequency component corresponds to one of the beat frequencies employed to elicit the fluorescence radiation from a particular location of the sample, the measure of the amplitude of the frequency component can provide a pixel value for a location associated with that frequency component along a horizontal row of the sample. In this manner, pixel values for an image of a horizontal row of the sample can be determined. The above steps can be repeated for fluorescence data obtained for each horizontal row of the sample as the sample flows through the flow cell in a vertical direction. The pixels values can be used to construct a fluorescence image (step 5).

Figure 12:
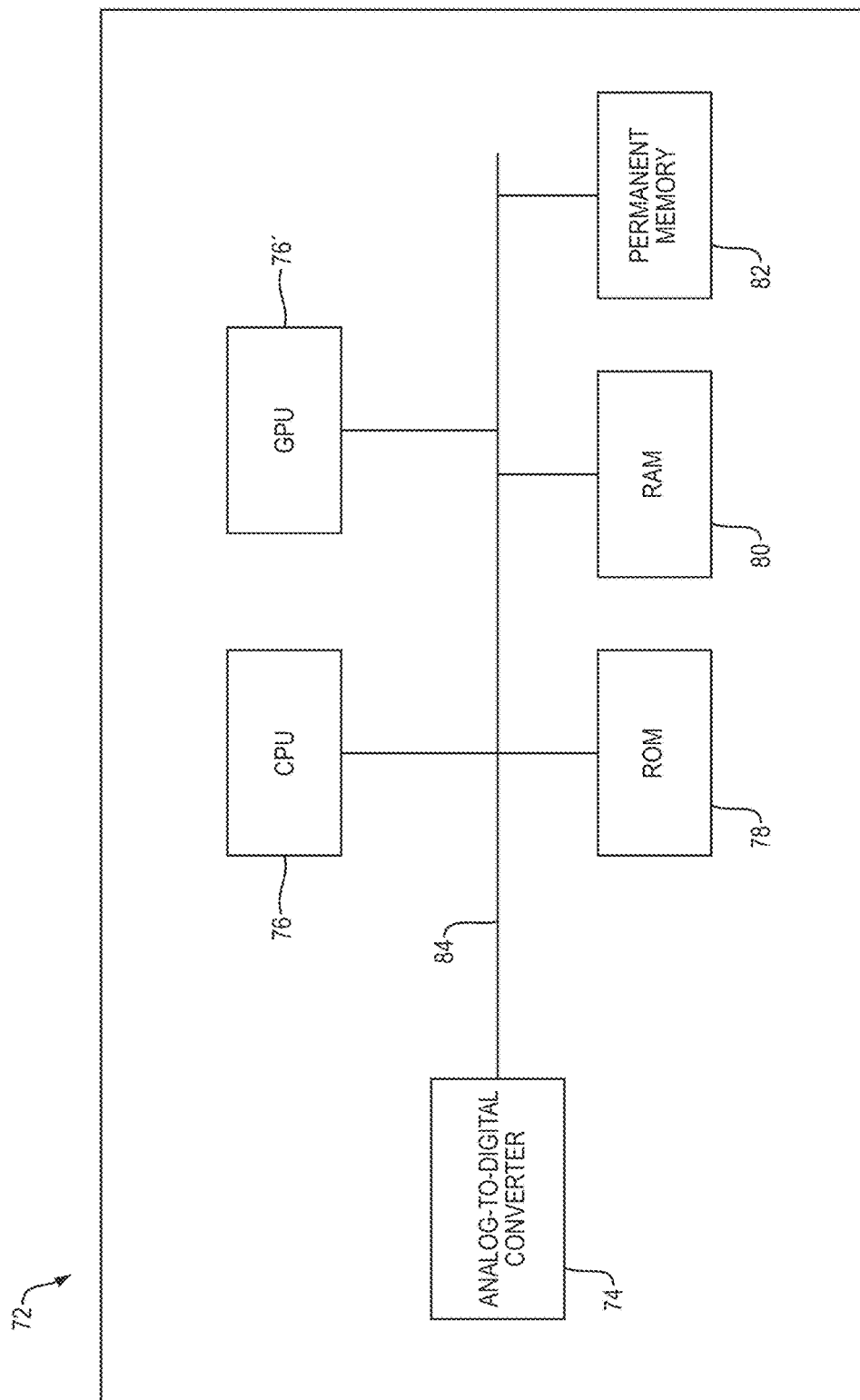

As noted above, the analysis module 72 can be implemented in hardware, firmware and/or software using techniques known in the art and in accordance with the present teachings. By way of example, FIG. 12 schematically depicts an exemplary implementation of analyzer 72, which includes an analog-to-digital converter 74 for receiving the amplified fluorescence signal from the amplifier 70 and digitizing that signal to generate digitized fluorescence data. The analysis module further includes a central processing unit (CPU) 76 for controlling the operation of the analysis module, including performing calculations and logic operations. The analysis module also includes ROM (read only memory) 78, RAM (random access memory) 80 and permanent memory 82. A communications bus 84 facilitates communication among various components of the analysis module, including communications between the CPU 76 and other components. The memory modules can be used to store instructions for analyzing the fluorescence data and the analysis results. By way of example, in some embodiments, instructions for data analysis, e.g., instructions for performing the above steps discussed in connection with FIGS. 11A and 11B, can be stored in the ROM 78. The CPU can employ instructions stored in ROM 78 to operate on digitized fluorescence data stored in RAM 80 to generate a fluorescence image of the sample (e.g., a one-dimensional or a two-dimensional image). The CPU can effect the storage of the fluorescence image in permanent memory 82, e.g., in a database. As shown schematically in FIG. 12, the analysis module can optionally include a graphics processing unit (GPU) 76' for performing calculations of pixel intensities and other quantities from the received data (e.g., fluorescence data).

Figure 13A:
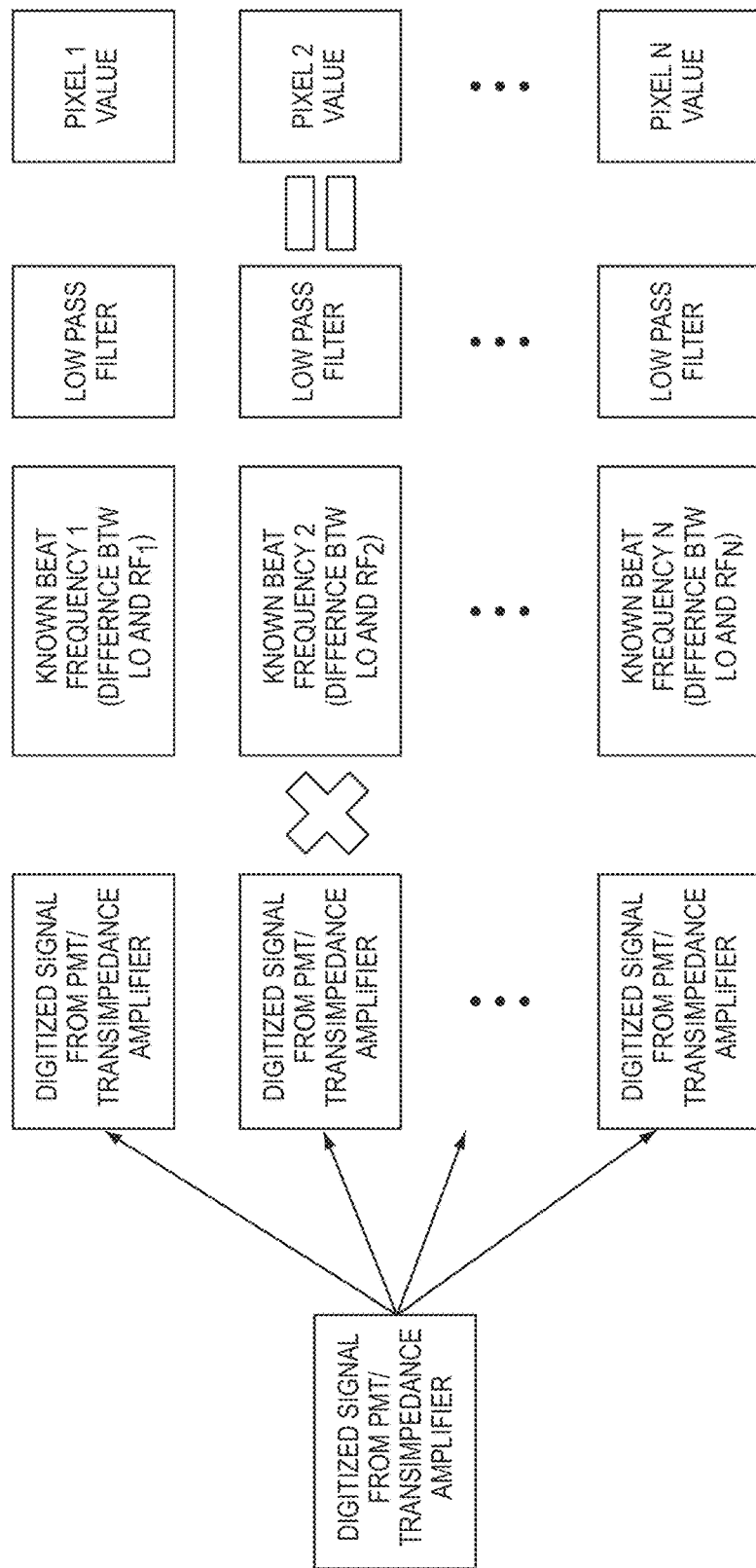
FIGS. 13A and 13B depict various steps in another method according to an embodiment of the invention for analysis of fluorescence signal obtained by illuminating a sample with a combined beam composed of a plurality of RF comb beams and a top-hat profiled LO beam.
Figure 13B:
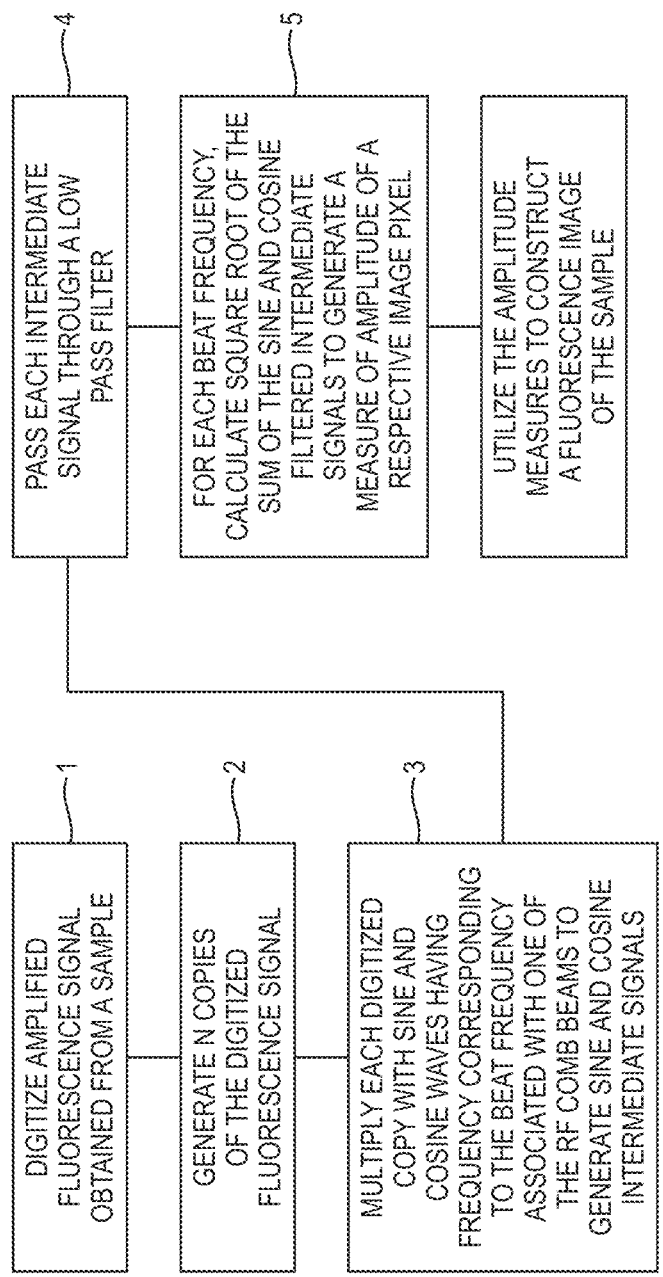

In some embodiments, the frequency demodulation of the output signal generated by the photodetector can be achieved using lock-in detection techniques. By way of example, with reference to FIGS. 13A and 13B, in one such embodiment, the amplified fluorescence signal is digitized (step 1) and several copies of the digitized fluorescence signal are generated (step 2), where the number (N) of the digitized copies corresponds to the number of frequencies associated with the RF comb beams. Each digitized copy of the signal is multiplied with sine and cosine waves having a frequency corresponding to a beat frequency equal to a difference between the frequencies of one of the RF comb beams and the LO beam to generate a plurality of intermediate signals (step 2). Each intermediate signal is passed through a low-pass filter (step 3), which has a bandwidth equal to one half of the frequency spacing between the RF comb frequencies.

For each beat frequency corresponding to one of the RF comb frequencies (in other words, for each frequency corresponding to a spatial location of the illuminated sample), square root of the sum of the squares of the two filtered intermediate signals corresponding to that frequency is obtained as a measure of the amplitude of an image pixel corresponding to the sample location illuminated by the LO beam and the RF comb beam having that frequency (step 4). In some embodiments, multiple fluorescence data signals corresponding to the same beat frequency (i.e., corresponding to the same sample location) can be processed in a manner discussed above and the pixel values can be averaged so as to obtain an average pixel value.

The above steps can be repeated for fluorescence data obtained for each horizontal row of the sample as the sample flows through the flow cell in a vertical direction. The pixels values can be used to construct a fluorescence image (step 5).

The above lock-in detection method can be implemented in software, firmware and/or hardware. By way of example, in one embodiment the above lock-in detection method can be implemented using a field programmable gate array (FPGA), particularly if more than 6 frequencies are used. In some embodiments, a multi-frequency lock-in amplifier, such as HF2L-MF multi-frequency amplifier marketed by Zurich Instruments of Zurich, Switzerland can be employed.

Figure 14A:
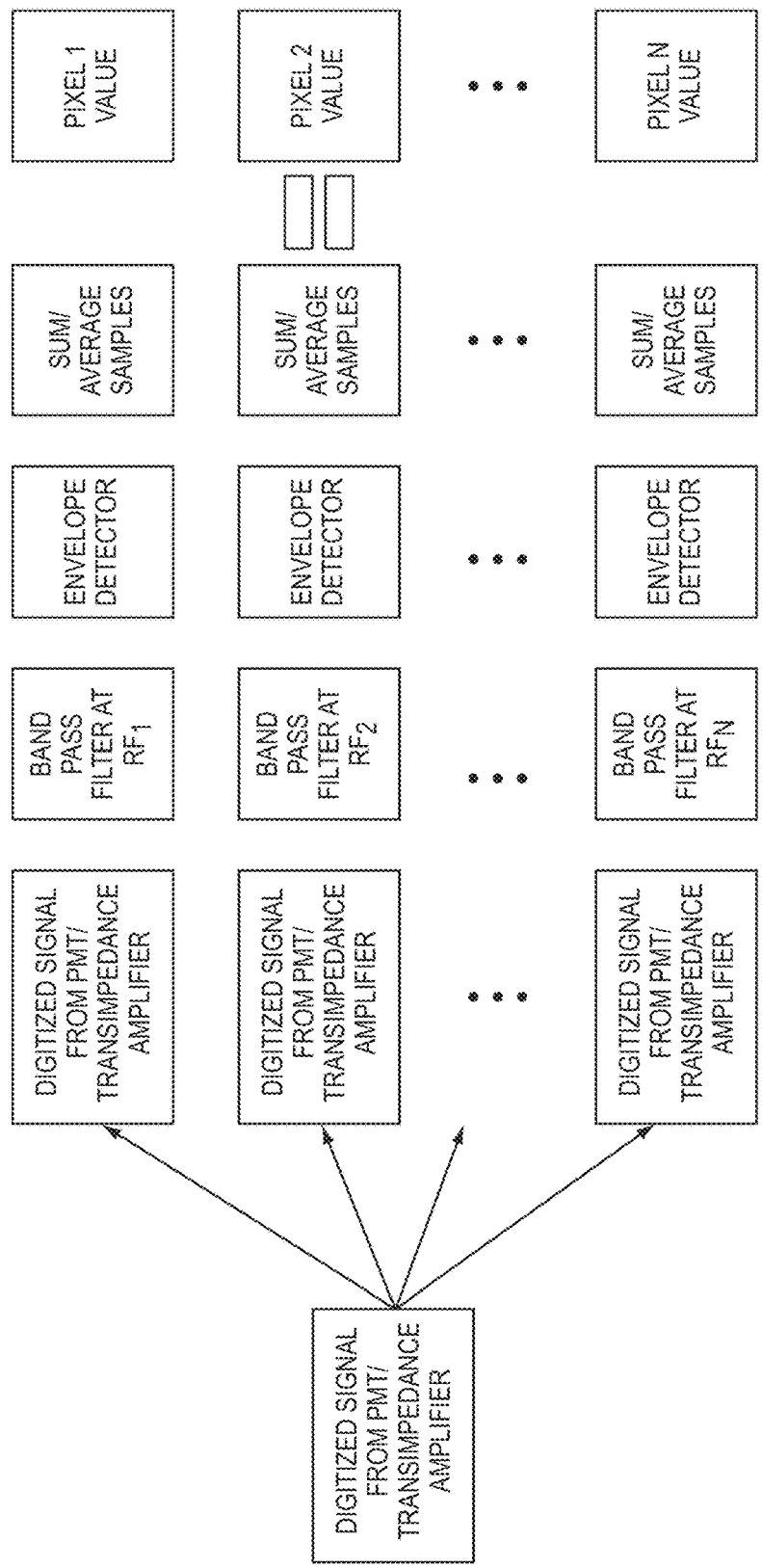
FIGS. 14A and 14B depict various steps in yet another method according to an embodiment of the invention for analysis of fluorescence signal obtained by illuminating a sample with a combined beam composed of a plurality of RF comb beams and a top-hat profiled LO beam, FIG. 15A schematically depicts illumination of a sample by a top-hat profiled beam at a single excitation frequency.
Figure 14B:
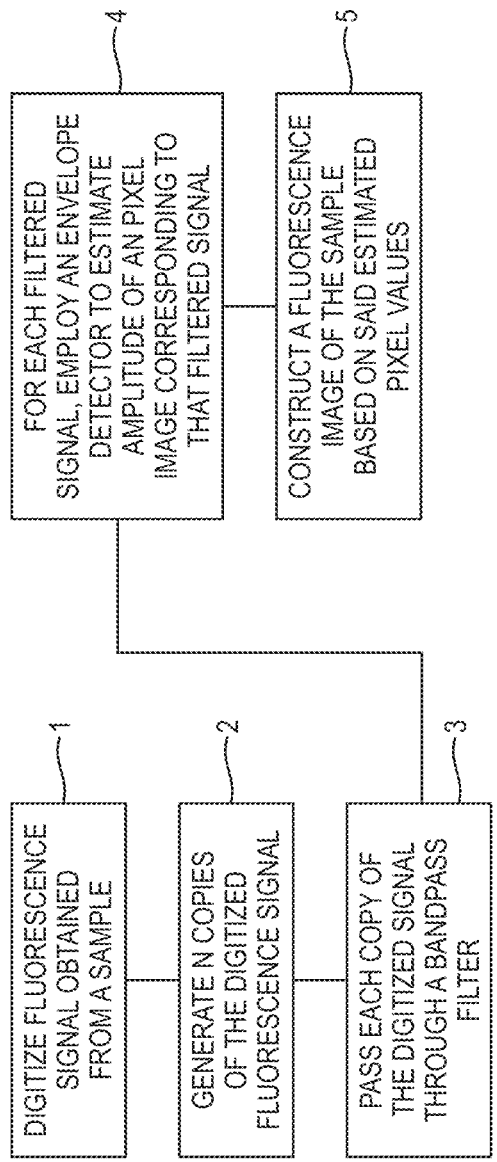

By way of further examples, in some embodiments the frequency demodulation of the detected fluorescence signal can be achieved by employing a bandpass filter-based image demodulation technique. By reference to FIGS. 14A and 14B, in one embodiment of such a frequency demodulation method, the fluorescence signal provided by the photodetector 64 and the amplifier 70 is digitized (step 1) and several copies of the digitized signal are generated (step 2), where the number (N) of the digitized copies corresponds to the number of frequencies associated with the RF comb beams. Each copy of the digitized fluorescence signal is filtered by passing that signal through a bandpass filter centered at a beat frequency associated with one of the RF comb beams (i.e., a beat frequency associated with a particular location of the sample) (step 3). More specifically, each bandpass filter is centered at one of N beat frequencies and has a bandwidth that is equal to half of the frequency spacing between adjacent beat frequencies.

An envelope detector at each beat frequency is employed to estimate, for each horizontal line, the amplitude of each pixel corresponding to that frequency (step 4). In some cases, a plurality of pixel values corresponding to a pixel, obtained by processing multiple fluorescent signals corresponding to a sample location associated with that pixel, is averaged to obtain an average pixel value. The above steps can be repeated for fluorescence data obtained for each horizontal row of the sample as the sample flows through the flow cell in a vertical direction. The pixels values can be used to construct a one-dimensional or a two-dimensional fluorescence image of the sample (step 5).

The analysis module can also be configured to receive and process the brightfield and darkfield image data. For example, with reference to FIG. 9C and FIG. 10, the analysis module 72 can be further configured to receive the darkfield and brightfield image data from photodetectors 208 and 218 to generate darkfield and brightfield images. For example, with reference to FIG. 12, the instructions for generating the darkfield and brightfield images, e.g., in a manner known in the art, can be stored in permanent memory 82. The processor 76 can employ these instructions to process the received darkfield and brightfield image data to generate the images. The analysis module can be also configured to generate composite images by overlaying, e.g., a fluorescence image and one or both of the brightfield and darkfield images.

The fluorescence images as well as the brightfield and darkfield images generated by a system according to the present teachings, such as the above system 10, can be used for a variety of different ways. For example, the fluorescence image can be integrated to produce a value comparable to the data produced by a conventional flow cytometer. The fluorescence image can also be analyzed to determine the location of fluorescent probe giving rise to that image (e.g., it can be determined whether the probe is the nucleus, cytoplasm, localized to organelles, or on the outside of the cell membrane). Further, in some applications, multiple fluorescent images obtained by detecting different fluorescent bands, all of which taken from the same cell, can be used to determine the degree of co-localization of multiple fluorescent probes within a cell. Additionally, the analysis of cell morphology, cell signaling, internalization, cell-cell interaction, cell death, cell cycle, and spot counting (e.g., FISH), among others, are possible using multi-color fluorescence, brightfield, and darkfield images.

As noted above, the system 10 can be operated in at least three different modes. In one mode discussed above, an LO beam and a plurality of RF comb beams concurrently illuminate a portion of the sample (e.g., locations disposed along a horizontal extent), and the fluorescence radiation emitted from the illuminated locations is detected and analyzed in order to construct a fluorescence image of the sample. In another operational mode, rather than applying a plurality of RF drive signals concurrently to the AOD, a frequency ramp containing the drive signals is applied to the AOD such that the frequency of the laser beam is changed over time from a start frequency ($f_1$) to an end frequency ($f_2$). For each drive frequency in the frequency ramp, the frequency of the laser beam is shifted by that drive frequency and the sample is illuminated by the frequency-shifted laser beam to elicit fluorescence radiation from the sample. In other words, in this mode, the system is operated to obtain fluorescence radiation from the sample by illuminating the sample successively over a temporal interval with a plurality of frequencies, which are shifted from the central laser frequency. The frequency shift generated by the AOD is accompanied by an angular deflection such that using the same optical path, the beam is scanned across the sample at a high speed.

More specifically, in this operational mode, the RF frequency synthesizer 10 is employed to ramp a drive signal applied to the AOD 18 from a start frequency ($f_1$) to an end frequency ($f_2$). By way of example, the frequency range over which the drive signal is ramped can be from about 50 MHz to about 250 MHz. In some embodiments, the drive signal is ramped from about 100 MHz to about 150 MHz. In this embodiment, the drive frequency is changed over time continuously, e.g., to achieve a high speed. In other embodiments, the drive frequency can be changed in discrete steps from a start frequency ($f_1$) to an end frequency ($f_2$).

The drive frequencies are chosen such that the frequency-shifted beam would miss the mirror 28 and propagate along an optical path defined by lens 26, lens 30, mirrors 40/42, a beam splitter 44, lens 46, mirror 56, lens 50, mirror 58 and the objective lens 52 to illuminate a portion of the sample flowing through the sample holder. The ramp rate is preferably fast enough so as to ameliorate and preferably prevent, any blur in the vertical direction of a fluorescence image to be generated based on the emitted fluorescence radiation as the sample flows across the beam. This can be achieved, for example, by matching the ramp rate with the sample's flow speed. The laser spot size at the sample can be used to estimate appropriate rates. By way of example, for a laser spot size of 1 micrometer, the scan time across 1 line should be 10 microseconds or less for a sample flow speed of 0.1 meters per second to avoid image blur.

The fluorescence radiation emitted from the sample in response to illumination by the excitation radiation is collected and detected in a manner discussed above. Specifically, with reference to FIG. 10, the fluorescence radiation is detected by photodetector 64. The detected fluorescence is amplified by the amplifier 70 and the amplified signal is analyzed by the analysis module 72 to reconstruct a fluorescence image of the sample. The reconstruction of the image is performed by assigning a horizontal pixel location to a specific time within the scan period from the start frequency ($f_1$) to the end frequency ($f_2$). As opposed to analyzing the amplitude of a frequency component to obtain pixel values as in the above operational mode, the demodulation approach used in this operational mode only uses the time domain values of the detected fluorescence signal to assign values to the pixels of the image. The process can be repeated as the sample flows in a vertical direction so as to obtain a two-dimensional fluorescence image of the sample.

The fluorescence radiation, if any, emitted by the sample is collected by photodetector 64. Referring to FIG. 10, the detected fluorescence radiation is amplified by the amplifier 70. The analysis module 72 receives the amplified signal. In this operational mode, the analysis module analyzes the fluorescence signal to determine the fluorescence content of the sample, e.g., a cell/particle. Since there is only one beam exciting the sample in this operational mode, no beat frequencies are generated in response to exciting the sample. Hence, there is no image information in the frequency domain of the fluorescence signal. Rather, the detected fluorescence signal has image information encoded in the time domain. In this operational mode, an image can be digitally reconstructed using the time values of the detected fluorescence signal as the horizontal pixel coordinate, and the digitized voltage values of the fluorescence signal as the pixel values (brightness). Each scan of the drive frequencies applied to the AOD produces one horizontal line (row) of the image. The image reconstruction is achieved via consecutive scans as the sample flows through the illumination area (point).

In yet another operational mode, the system 10 can be operated to illuminate a plurality of locations of a sample concurrently by a single excitation frequency, which can be generated, e.g., by shifting the central frequency of a laser beam by a radiofrequency. More specifically, referring again to FIG. 1, in such an operational mode a single drive radio frequency can be applied to the AOD 18 to generate a laser beam having a frequency that is shifted relative to the laser beam entering the AOD 18. Further, the frequency-shifted laser beam exhibits an angular shift relative to the laser beam entering the AOD such that the radiofrequency laser beam is intercepted and reflected by the mirror 28 towards the top-hat beam shaper 34 via lens 32 and mirrors 33 and 35. The beam exiting the top-hat beam shaper is reflected by the beam splitter 44 and is focused by the lens 46 onto the intermediate image plane 48. In this plane, as shown schematically in FIG. 15A, the laser beam 1000 shows a stretched profile along the horizontal direction.

The horizontally-stretched laser beam is reflected by the mirror 56 to the positive lens 50. After passage through the lens 50, the laser beam is reflected by the mirror 58 to the objective lens 52. As discussed above, the positive lens 50 and the objective lens 52 form a telescope for relaying the top-hat profiled laser beam from the intermediate image plane 48 onto a sample flowing through the flow cell 54.

The horizontally-stretched laser beam illuminates a horizontal extent of the sample to excite a fluorophore of interest, if present in the sample, along that horizontal extent. Thus, in this operational mode, unlike the first operational mode in which a plurality of horizontal locations of the sample is illuminated at different excitation frequencies, a plurality of horizontal locations of the sample is illuminated at the same excitation frequency. This operational mode does not enable a user to obtain an image of cells or particles that flow by. However, in this operational mode, a higher optical power can typically be applied to the sample than in the other two operational modes, which can be useful for obtaining a higher signal-to-noise ratio data if images are not required. This operational mode is accessible by merely altering the electronic signal driving the acousto-optic deflector, without a need to make any mechanical changes to the system.

Thus, the system 10 can be operated in three distinct operational mode to elicit fluorescence radiation from a sample.

Figure 15B:
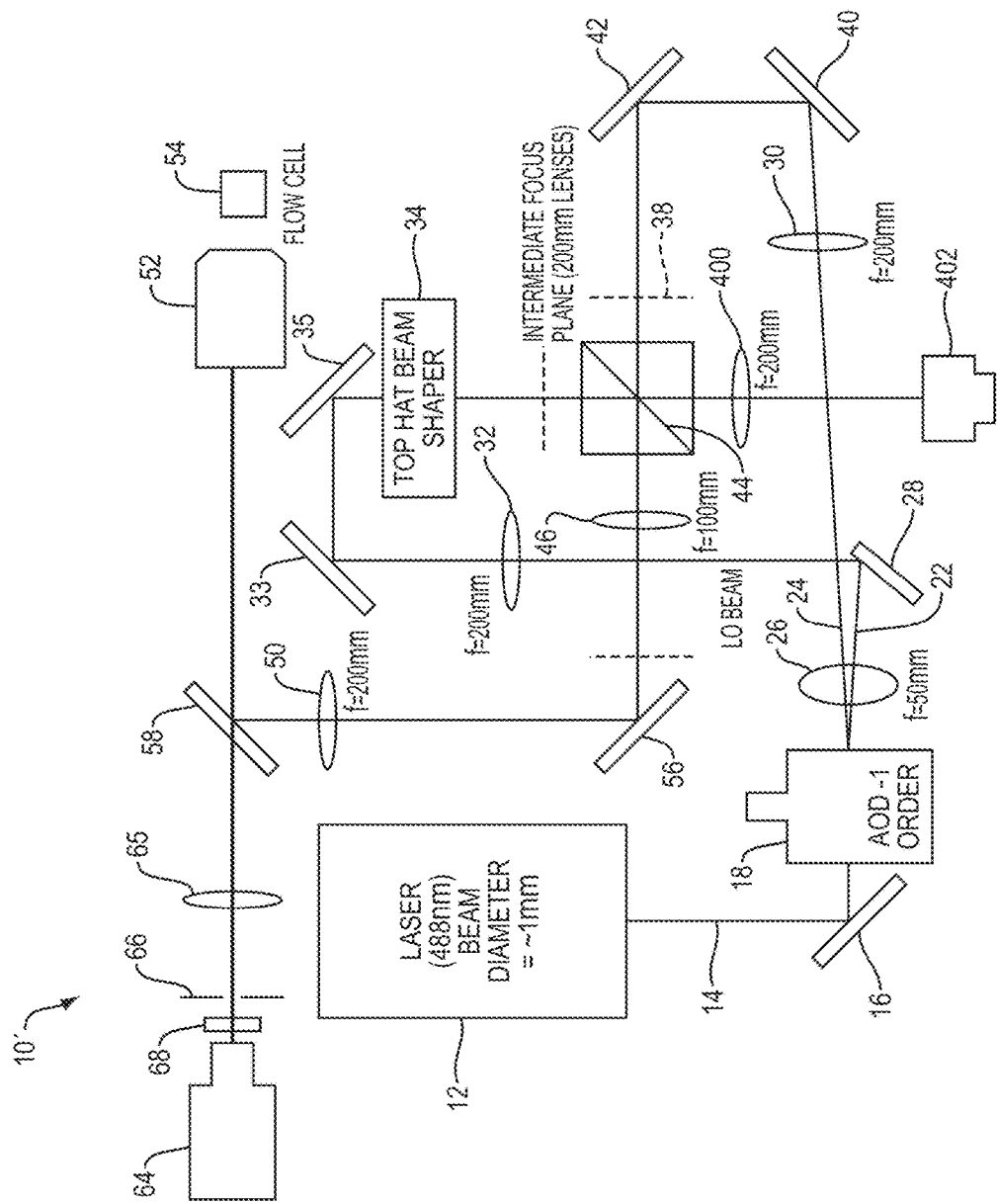
FIG. 15B is a schematic view of a system according an embodiment of the present teachings that allows for fluorescence lifetime measurements and fluorescence lifetime imaging.

In some embodiments, fluorescence lifetime measurements can be performed at each spatial position on the sample, e.g., by comparing the phase of the beats of each of the radiofrequency-shifted and local oscillator beams with the phase of a respective radiofrequency component in the detected fluorescence signal. By way of example, FIG. 15B shows a system 10', a modified version of the system 10 discussed above, that allows for such fluorescence lifetime measurements (certain components shown in FIG. 1 are not depicted in this figure for brevity). Specifically, a portion of the RF comb beams incident on the beam splitter 44 is reflected by the beam splitter onto a convergent lens 400 (by way of illustration in this embodiment the lens 400 has a focal length of 200 mm, though other focal lengths can also be used). The lens 400 focuses that portion of the RF comb beams onto a photodiode 402, which detects the excitation beam. The output of the photodiode 402 can be received by the analysis module 72 (See, FIG. 10). The analysis module can provide frequency de-multiplexing of the excitation beam, e.g., using one of the de-modulation techniques discussed above and determine the phase of each radio frequency component in the excitation beam. This can provide, for each radiofrequency component in the detected fluorescence signal, a reference phase with which the phase of that radiofrequency component can be compared. For example, the real and imaginary components of an FFT of the excitation signal or the I and Q components of lock-in type demodulation can be employed. Alternatively, the output of the detector detecting the brightfield image of the sample/flow cell can be used to obtain reference phases with which the phases of the fluorescence beat frequencies can be compared.

More specifically, the analysis module 72 can provide frequency de-multiplexing of the detected fluorescence signal, e.g., in a manner discussed above. As will be appreciated by one skilled in the art, for each beat frequency in the fluorescence signal, the phase of the radiofrequency component can be compared with the respective reference phase of the excitation beam to obtain spatially-resolved fluorescence lifetime measurements and a fluorescence lifetime image.

In certain embodiments, the subject systems include flow cytometer systems employing the optical configurations described above for detecting light emitted by a sample in a flow stream. In certain embodiments, the subject systems are flow cytometer systems which include one or more components of the flow cytometers described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300; 8,233,146; 8,753,573; 8,975,595; 9,092,034; 9,095,494 and 9,097,640; the disclosures of which are herein incorporated by reference.

As described above, in some embodiments the subject systems are configured for imaging particles (e.g., cells) in sample flowing a flow stream, such as in the flow stream of a flow cytometer. The flow rate of particles in the flow stream may be 0.00001 m/s or more, such as 0.00005 m/s or more, such as 0.0001 m/s or more, such as 0.0005 m/s or more, such as 0.001 m/s or more, such as 0.005 m/s or more, such as 0.01 m/s or more, such as 0.05 m/s or more, such as 0.1 m/s or more, such as 0.5 m/s or more, such as 1 m/s or more, such as 2 m/s or more, such as 3 m/s or more, such as 4 m/s or more, such as 5 m/s or more, such as 6 m/s or more, such as 7 m/s or more, such as 8 m/s or more, such as 9 m/s or more, such as 10 m/s or more, such as 15 m/s or more and including 25 m/s or more. For example, depending on the size of the flow stream (e.g., the flow nozzle orifice), the flow stream may have a flow rate in the subject systems of 0.001 µL/min or more, such as 0.005 µL/min or more, such as 0.01 µL/min or more, such as 0.05 µL/min or more, such as 0.1 µL/min or more, such as 0.5 µL/min or more, such as 1 µL/min or more, such as 5 µL/min or more, such as 10 µL/min or more, such as 25 µL/min or more, such as 50 µL/min or more, such as 100 µL/min or more, such as 250 µL/min or more and including 500 µL/min or more.

The following examples are provided solely for further elucidation of various aspects of the present teachings and are not intended to illustrate necessarily the optimal ways of implementing the teachings of the invention or the optimal results that can be obtained.

Example 1

A system similar to that described above in connection with FIG. 1 with a detection system similar to that described above in connection with FIG. 9A was employed to measure fluorescence radiation from polystyrene beads stained with 8 discrete levels of fluorescence dyes, which are marketed by Spherotech Inc. of Lake Forest, Ill. under tradename RCP-30-5A. The system was also used to generate bright-field and darkfield images in a manner discussed above.

FIG. 16A is a scatter plot of darkfield intensity versus brightfield intensity. The rectangular section of the plot was used as a gate to generate the data depicted in FIGS. 16B, 16C, and 16D, which contains about 32% of all events measured (50,000 total events were detected). FIG. 16B shows a scatter plot of the red fluorescence (PI) v. green fluorescence (FITC) emitted by each particle. This plot clearly shows 8 populations with varying levels of brightness. FIGS. 16C and 16D are histograms of the same data.

Example 2

FIRE, brightfield, and darkfield images of fixed peripheral blood leukocytes stained with CD45-FITC and propidium iodide were obtained using a system similar to that described above in connection with FIG. 1 with a detection system similar to that discussed above in connection with FIG. 9A. The sample also contained a fraction of live HeLa cells, stained with Calcein-AM. The cells were flowing through the flow cell at a rate of 0.5 meters/second during data acquisition.

Figure 17A:
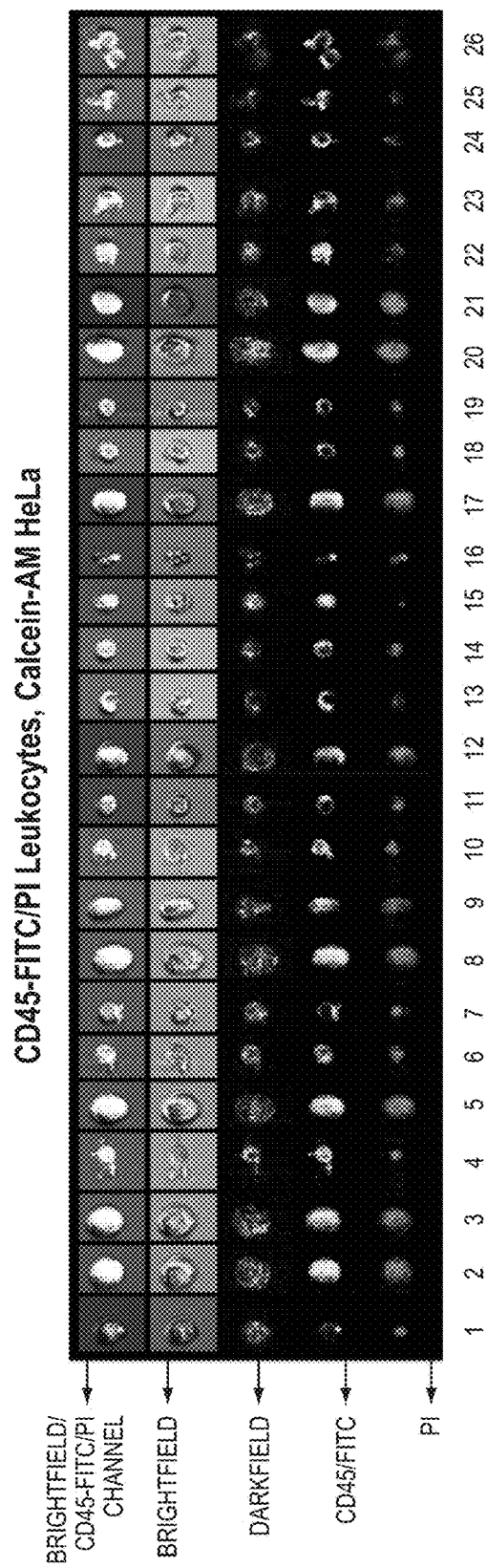
FIG. 17A shows brightfield, darkfield and fluorescence images of a sample containing fixed peripheral blood leukocytes stained with anti-CD45-FITC, and propidium iodide obtained using a cytometry system according to the present teachings, where the sample also contained a fraction of live HeLa cells that were stained with Calcein-AM.

The images shown in FIG. 17A are from top to bottom: overlay of bright-field, CD45-FITC, and propidium iodide fluorescence channels, bright-field, dark-field, CD45-FITC, and PI channel fluorescence. No compensation has been applied, and all images are auto-scaled for viewing. Cells numbered 2, 3, 5, 8, 9, 12, 17, 20, and 21 are HeLa cells (B population), and the others are leukocytes (A population).

Figure 17B:
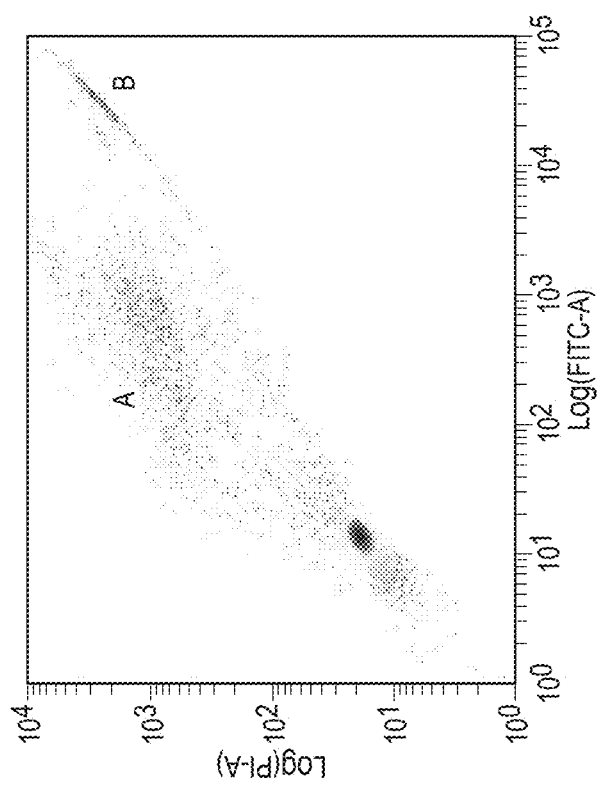
FIG. 17B is a scatter plot in which population A represents leukocytes and population B represents HeLa cells in the sample for which FIG. 17A provides images.

FIG. 17B is a scatter plot in which population A represents leukocytes and population B represents HeLa cells.

Example 3

FIRE, brightfield, and darkfield images of fixed peripheral blood leukocytes stained with CD45-FITC and propidium iodide were obtained using a system similar to that described above in connection with FIG. 1 with a detection system similar to that discussed above in connection with FIG. 9A. The sample was spiked with a small fraction of fixed MCF-7 cells, stained with anti-EpCAM-FITC and propidium iodide (PI). The cells were flowing through a flow cell at a rate of 0.5 meters/second during data acquisition.

Figure 18A:
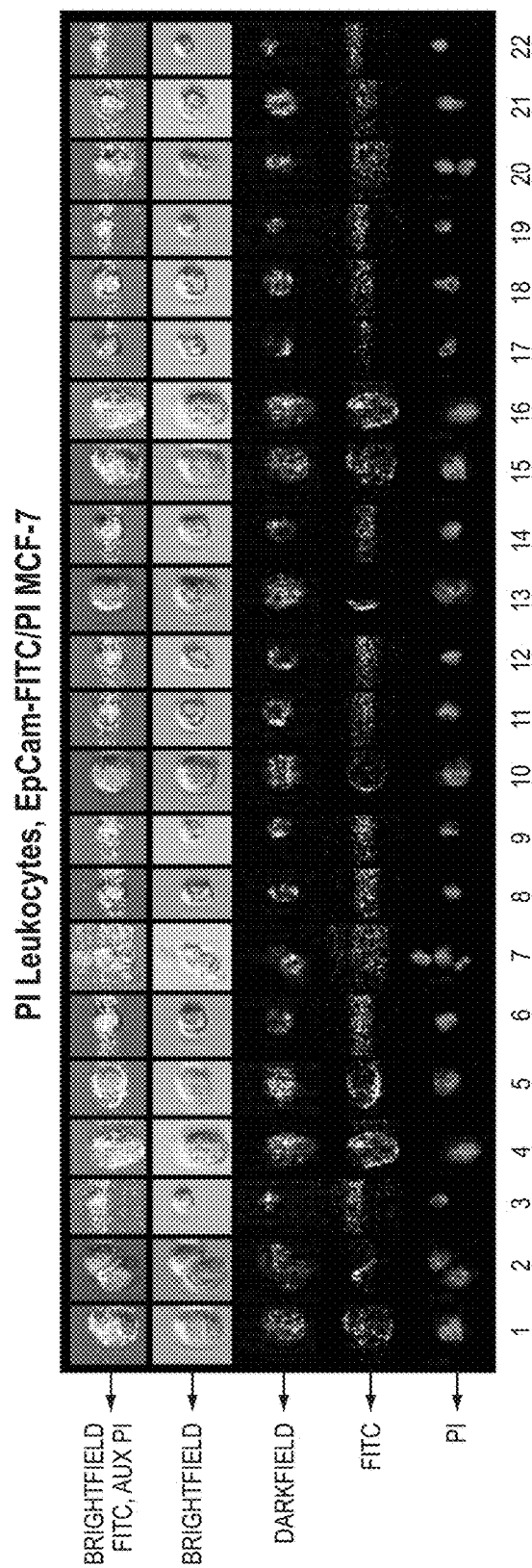
FIG. 18A shows brightfield, darkfield and fluorescence images of a sample containing fixed peripheral blood leukocytes stained with anti-CD45-FITC and propidium iodide obtained using a cytometry system according to an embodiment of the present teachings, where the sample was spiked with a small fraction of fixed MCF-7 cells stained with anti-EpCAM-FITC and propidium iodide.

The images shown in FIG. 18A are from top to bottom: an overlay of brightfield, FITC, and PI channel fluorescence, brightfield, darkfield, FITC, and PI fluorescence. In the leukocyte population, green fluorescence is an artifact of fluorescence spillover from the PI stain. All images were auto-scaled in brightness for viewing, and thus, leukocytes appear to exhibit FITC fluorescence, yet this is a small fluorescence spillover signal from the PI. Cells numbered as 1, 2, 4, 5, 10, 13, 15, and 16 are MCF-7 cells.

Figure 18B:
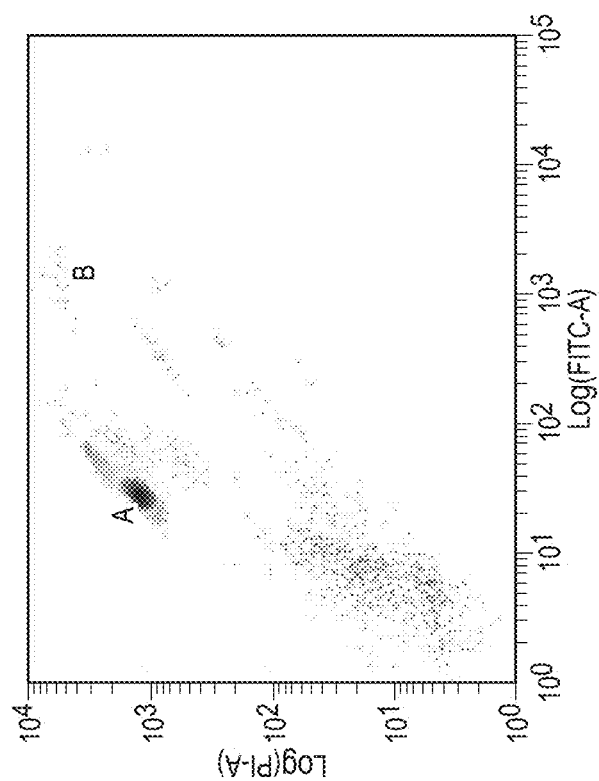
FIG. 18B is a scatter plot in which population A represents leukocytes and population B represents MCF-7 cells in the sample for which FIG. 18A provide images.

FIG. 18B is a scatter plot in which population A represents leukocytes, and population B represents MCF-7 cells.

Those having ordinary skill in the art will appreciate that various changes can be made without departing from the scope of the present teachings. In particular, various features, structures, or characteristics of embodiments discussed above can be combined in a suitable manner. For example, the detection systems discussed in connection with one embodiment may be used in another embodiment.

The invention claimed is:

1. A method comprising:
    applying a radiofrequency drive signal to an acousto-optic device;
    irradiating the acousto-optic device with a laser to generate a first angularly deflected laser beam and a second angularly deflected laser beam;
    propagating the first angularly deflected laser beam along a different optical path from the second angularly deflected laser beam; and
    combining the first angularly deflected laser beam with the second angularly deflected laser beam and directing the combined laser beam onto a sample; and
    detecting one or more light signals from the sample.

2. The method according to claim 1, wherein acousto-optic device is an acousto-optic deflector.

3. The method according to claim 1, wherein the first angularly deflected laser beam comprises a local oscillator (LO) beam and the second angularly deflected laser beam comprises a plurality of radiofrequency comb beams.

4. The method according to claim 3, wherein the method comprises propagating the local oscillator beam through a top-hat beam shaper to produce a local oscillator beam with a substantially constant intensity profile along a horizontal axis.

5. The method according to claim 4, wherein the local oscillator beam has a Gaussian intensity profile along a vertical axis.

6. The method according to claim 4, wherein the plurality of radiofrequency comb beams each have a Gaussian intensity profile along the horizontal axis.

7. The method according to claim 1, wherein each of the plurality of radiofrequency comb beams irradiates a different spatial location on the sample.

8. The method according to claim 7, wherein each of the plurality of radiofrequency comb beams overlaps with the local oscillator beam on the sample.

9. The method according to claim 8, wherein fluorescence from the sample at each overlap location exhibits a beat frequency that comprises a frequency difference between the local oscillator beam and the radiofrequency comb beam.

10. The method according to claim 8, further comprising modulating the intensity of each of the radiofrequency comb beams.

11. The method according to claim 10, wherein modulating the intensity of the radiofrequency comb beams comprises adjusting the intensity of each radiofrequency comb beam to be equal to the intensity of the local oscillator beam.

12. The method according to claim 11, wherein the detected light signal comprises a time-domain fluorescence emission signal.

13. The method according to claim 12, further comprising generating an image of the sample based on a plurality of time-domain fluorescence emission signals.

14. The method according to claim 13, wherein generating the image comprises frequency de-multiplexing each fluorescence emission signal to determine the beat frequencies at each overlap location on the sample.

15. The method according to claim 14, wherein frequency de-multiplexing comprises obtaining a Fourier Transform of the fluorescence signal to determine the beat frequency at each overlap location on the sample.

16. The method according to claim 15, wherein generating the image comprises computing the amplitude of each beat frequency to provide a pixel value corresponding to a location of the image.

17. The method according to claim 16, wherein generating the image comprises generating a darkfield image of the sample and generating a brightfield image of the sample.

18. The method according to claim 1, wherein the sample is present in a flow stream.

19. The method according to claim 18, wherein the flow stream has a flow rate of particles of 1 m/s or more.

* * * * *

UNITED STATES PATENT AND TRADEMARK OFFICE
CERTIFICATE OF CORRECTION

PATENT NO. : 10,288,546 B2
APPLICATION NO. : 16/058734
DATED : May 14, 2019
INVENTOR(S) : Eric D. Diebold et al.

Page 1 of 1

It is certified that error appears in the above-identified patent and that said Letters Patent is hereby corrected as shown below:

In the Specification

Column 1, Line 8, please replace "Application No. 62/240,894, filed Oct. 13. 2016, the con-" with
-- Application No. 62/240,894, filed Oct. 13. 2015, the con- --

Signed and Sealed this
Second Day of June, 2020

Andrei Iancu
*Director of the United States Patent and Trademark Office*